(12) United States Patent
Bromberg et al.

(10) Patent No.: US 8,992,985 B2
(45) Date of Patent: Mar. 31, 2015

(54) CORE-SHELL MAGNETIC PARTICLES AND RELATED METHODS

(75) Inventors: Lev E. Bromberg, Swampscott, MA (US); Emily P. Chang, Edison, NJ (US); Trevor Alan Hatton, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/289,515

(22) Filed: Nov. 4, 2011

(65) Prior Publication Data

US 2012/0135080 A1 May 31, 2012

Related U.S. Application Data

(60) Provisional application No. 61/410,695, filed on Nov. 5, 2010.

(51) Int. Cl.
*A61K 9/16* (2006.01)
*A01N 25/12* (2006.01)
*B03C 1/015* (2006.01)
*B03C 1/30* (2006.01)
*B82Y 30/00* (2011.01)
*B82Y 40/00* (2011.01)
*H01F 1/00* (2006.01)
*H01F 1/44* (2006.01)

(52) U.S. Cl.
CPC ............... *A01N 25/12* (2013.01); *B03C 1/015* (2013.01); *B03C 1/30* (2013.01); *B03C 2201/26* (2013.01); *B82Y 30/00* (2013.01); *B82Y 40/00* (2013.01); *H01F 1/0054* (2013.01); *H01F 1/445* (2013.01)
USPC .......................................... 424/490; 424/489

(58) Field of Classification Search
None
See application file for complete search history.

(56) References Cited

U.S. PATENT DOCUMENTS

| 6,548,264 | B1 | 4/2003 | Tan et al. |
| 7,524,630 | B2 | 4/2009 | Tan et al. |
| 7,795,041 | B2 | 9/2010 | Hatton et al. |
| 8,337,813 | B2 * | 12/2012 | Schultz Sikma et al. .... 424/9.34 |
| 2007/0140974 | A1 * | 6/2007 | Torres et al. ............... 424/9.323 |

FOREIGN PATENT DOCUMENTS

| WO | WO 2011/023430 A1 * | 3/2011 |
| WO | WO 2011023430 A1 * | 3/2011 |

OTHER PUBLICATIONS

Huang C et al., Silica-coated magnetic nanoparticles modified with gamma-mercaptopropyltrimethoxysilane for fast and selective solid phase extraction of trace amounts of Cd, Cu, Hg, and Pb in environmental and biological samples prior to their determination by inductively coupled plasma mass spectrometry. *Spectrochimica Acta Part B* 63:437-444 (2008).

(Continued)

*Primary Examiner* — Anand Desai
*Assistant Examiner* — Melissa Mercier
(74) *Attorney, Agent, or Firm* — Dana M. Gordon; Foley Hoag LLP

(57) ABSTRACT

The invention provides core-shell magnetic particles comprising a magnetic core and a functional shell, methods for making same, methods of separation using same, methods for using same, and devices comprising same. The particles and methods of the invention are useful for targeting and removing substances of interest that may be found in complex mixtures.

13 Claims, 9 Drawing Sheets

(56) References Cited

OTHER PUBLICATIONS

Huang Y-F et al., Amine-functionalized magnetic nanoparticles for rapid capture and removal of bacterial pathogens. *Environ. Sci. Technol.* 44(20):7908-7913 (2010).

Ma Z et al., Superparamagnetic silica nanoparticles with immobilized metal affinity ligands for protein adsorption. *J. Magnetism Magnetic Materials* 301:469-477 (2006).

Invitation to Pay Additional Fees and Partial International Search Report issued in corresponding International Application No. PCT/US2011/059313, dated Dec. 6, 2012.

* cited by examiner

1. Synthesis of magnetite by Fe(II)/Fe(III) chloride coprecipitation, redispersion with 15 wt% TMAOH 2. Encapsulation 3. Attachment of PEI 4. Thiolation 1. Synthesis of magnetite by Fe(II)/Fe(III) chloride coprecipitation, redispersion with 15 wt% TMAOH 2. Encapsulation 3. Attachment of PHMBG

CORE-SHELL MAGNETIC PARTICLES AND RELATED METHODS

RELATED APPLICATION

This application claims benefit under 35 U.S.C. §119(e) of U.S. provisional patent application No. 61/410,695, filed on Nov. 5, 2010.

GOVERNMENT SUPPORT

This invention was made with government support under Contract No. HDTRA1-09-01-0012 awarded by the Defense Threat Reduction Agency (DTRA). The government has certain rights in the invention.

BACKGROUND OF THE INVENTION

This invention is in the area of processes and materials, and encompasses particles whose dispersion in aqueous media results in environmental benefits and which are removable from the environment by means of applied magnetic field. The particles possess a core/shell structure with a magnetic core and a functional shell.

Magnetic separation is a means by which complex separations may be accomplished. In this context, functional magnetic-particles in aqueous solution, termed magnetic fluids, have found particular use. The application of high gradient magnetic separation (HGMS), which uses a magnetic field to separate magnetic particles from suspension, has been exploited such that when these particles are attached to biological materials of interest (e.g., cells, drugs), the material of interest or target material may thereby be separated from other materials not bound to the magnetic-particles.

Functional magnetic nanoparticles that are separated using a magnetic field have been described in U.S. Pat. No. 7,795,041 to Hatton et al., the content of which is incorporated herein by reference in its entirety. However, thus described magnetic nanoparticles directly embedded into and non-covalently bound with a polymer matrix comprising one or multiple polymers are lacking in chemical stability, which leads to the loss of magnetization of the particles over time and particle dissolution under conditions of the environment.

U.S. Pat. No. 7,524,630 to Tan et al. the content of which is incorporated herein by reference in its entirety, describes nanoparticles having a core/shell structure with a magnetic core and a silicon oxide shell functionalized with biologically active molecules such as antibodies and nucleotides. The nanoparticles of U.S. Pat. No. 7,524,630 are disclosed to be useful to label cells, to detect and isolate nucleic acid molecules having specific nucleotide sequences, and to separate a mixture of different nucleic acid molecules. More specifically, U.S. Pat. No. 7,524,630 discloses a pre-formed silica surface being conjugated with at least one functional group comprising an oligonucleotide in the form of a molecular beacon, wherein the sequence of said oligonucleotide comprises a single-stranded loop structure comprising a nucleic acid sequence of interest. However, biologically active molecules such as nucleotides or antibodies conjugated to the particle surface are rapidly consumed and degraded by deleterious compounds present in the environment and thus cannot be used for aqueous remediation and as synthetic antiseptics.

U.S. Pat. No. 6,548,264 to Tan et al. discloses silica-coated nanoparticles and a process for producing silica-coated nanoparticles. Silica-coated nanoparticles in accordance with U.S. Pat. No. 6,548,264 are prepared by precipitating nano-sized cores from reagents dissolved in the aqueous compartment of a water-in-oil microemulsion. A reactive silicate is added to coat the cores with silica. The method employs a microemulsion, i.e., isotropic and thermodynamically stable single-phase system, to produce nanoparticles cores of a predetermined, very uniform size and shape. Cores produced using the microemulsion are then coated with silica using a silicating agent. The nanoparticles thus formed can be customized for a particular application by derivatizing various chemical groups onto the pre-formed silica coating. However, the microemulsion synthesis of the nanoparticles in accordance with U.S. Pat. No. 6,548,264 is cumbersome and cannot be readily scaled up and requires purification of the particles from the surfactant employed to create the microemulsion in the first place.

SUMMARY OF THE INVENTION

The present invention relates to polymer nanoparticles, methods for their preparation, and their use as, for example, antiseptics for fish farming, devices for in-situ biodefense, removal of toxic pollutants from natural and artificial water sources, soil, and sediments. The invention advantageously provides several mechanisms for surface modifications, functionalization, and general characteristic tailoring to improve performance in antiseptics, in-situ biological and chemical defense, and removal of toxic pollutants.

In the present invention, the shell encapsulates the core to protect against oxidation and dissolution. The nanoparticles are preferably above 50 nm in size for easy capture by magnet not impeded by Brownian motion.

In contrast to U.S. Pat. No. 7,524,630 to Tan et al., the present invention utilizes synthetic polymeric and monomeric functional groups not susceptible to hydrolytic degradation by nucleases and proteases and other enzymes capable of degrading biologically active molecules.

In contrast to U.S. Pat. No. 6,548,264 to Tan et al., the methods described in the present invention do not utilize surfactants or miniemulsions. Instead, pre-formed iron oxide particles are directly encapsulated by functional silica shell incorporating silanes having at least one chemical group that is reactive with functional groups that can be covalently bound to the silicone oxide layer. Such groups can be electrophilic group or a nucleophilic group, including epoxy, alkyl halide, ester, aldehyde, ketone, amine, imine, amide, oxime, thiol, hydroxyl, alkenyl, carboxyl, and the like.

An aspect of the invention is a particle, comprising a plurality of magnetic nanoparticles, and a silicon oxide shell surrounding the plurality of magnetic nanoparticles, wherein the silicon oxide shell integrally comprises a plurality of functionalized alkyl silanes, wherein each functionalized alkyl silane comprises a reactive functional group selected from the group consisting of an electrophilic group and a nucleophilic group.

In one embodiment the magnetic nanoparticles comprise magnetite.

In one embodiment the reactive functional group is an electrophilic group. In one embodiment the electrophilic group is selected from the group consisting of epoxy, alkyl halide, ester, aldehyde, and ketone.

In one embodiment the first reactive functional group is a nucleophilic group. In one embodiment the nucleophilic group is selected from the group consisting of amine, imine, amide, oxime, thiol, hydroxyl, alkenyl, and carboxyl.

An aspect of the invention is a particle, comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

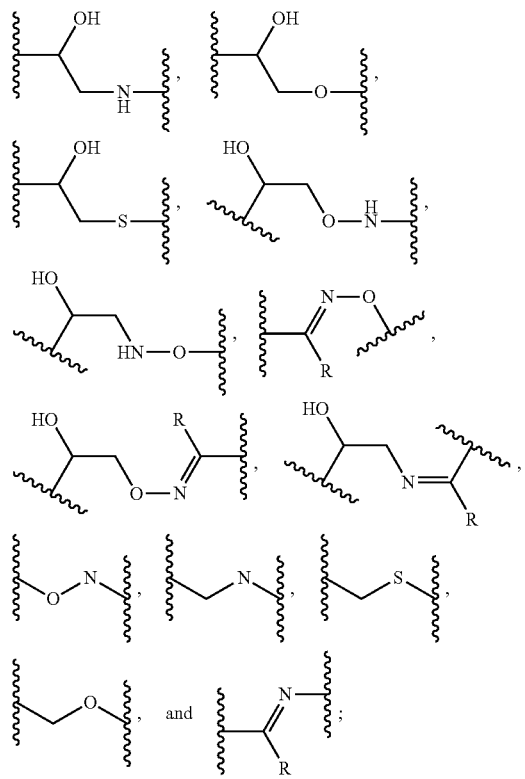

and $FG^3$ is a reactive functional group covalently linked to $L^2$ and selected from the group consisting of an electrophilic group and a nucleophilic group.

In one embodiment the magnetic nanoparticles comprise magnetite.

In one embodiment $FG^3$ is an electrophilic group. In one embodiment the electrophilic group is selected from the group consisting of epoxy, alkyl halide, ester, aldehyde, and ketone.

In one embodiment $FG^3$ is a nucleophilic group. In one embodiment the nucleophilic group is selected from the group consisting of amine, imine, amide, oxime, thiol, hydroxyl, alkenyl, and carboxyl.

In one embodiment $L^2$-$FG^3$ is a polymer.

In one embodiment the polymer is polyethyleneimine (PEI).

In one embodiment the polymer is poly(hexamethylene biguanide).

An aspect of the invention is a method for producing a particle. The method includes the step of combining (i) an aqueous solution of magnetic nanoparticles with (ii) a reactive silicate and (iii) a functionalized alkyl silane comprising a reactive functional group selected from the group consisting of an electrophilic group and a nucleophilic group, under conditions permitting formation of the silicon oxide shell surrounding the magnetic nanoparticles and integrally comprising the functionalized alkyl silane.

In one embodiment the magnetic nanoparticles comprise magnetite.

In one embodiment the reactive silicate is tetraethyoxysilane (TEOS).

In one embodiment the functionalized alkyl silane comprising the reactive functional group is aminopropyltrimethoxysilane (APTS).

In one embodiment the reactive functional group is an electrophilic group. In one embodiment the electrophilic group is selected from the group consisting of epoxy, alkyl halide, ester, aldehyde, and ketone.

In one embodiment the reactive functional group is a nucleophilic group. In one embodiment the nucleophilic group is selected from the group consisting of amine, imine, amide, oxime, thiol, hydroxyl, alkenyl, and carboxyl.

In one embodiment the functionalized alkyl silane comprising the reactive functional group is 3-glycidoxypropyltrimethoxysilane (GPTMS).

An aspect of the invention is a method for producing a particle. The method includes the steps of combining (i) an aqueous solution of magnetic nanoparticles, (ii) a reactive silicate, and (iii) a functionalized alkyl silane comprising a first reactive functional group selected from an electrophilic group or a nucleophilic group, under conditions permitting the formation of the silicon oxide shell surrounding the magnetic nanoparticles and integrally comprising the functionalized alkyl silane; and linking the functionalized alkyl silane to a molecule comprising a second reactive functional group through a covalent bond formed by reaction of the first reactive functional group with the second reactive functional group, wherein the second reactive functional group is (i) complementary to the first reactive functional group and (ii) selected from the group consisting of an electrophilic group and a nucleophilic group In one embodiment the magnetic particles are stabilized with tetramethylammonium hydroxide (TMAOH).

In one embodiment the magnetic nanoparticles comprise magnetite.

In one embodiment the reactive silicate is tetraethyoxysilane (TEOS).

In one embodiment the functionalized alkyl silane comprising the reactive functional group is aminopropyltrimethoxysilane (APTS).

In one embodiment the first reactive functional group is an electrophilic group and the second reactive functional group is a nucleophilic group. In one embodiment the electrophilic group is selected from the group consisting of epoxy, alkyl halide, ester, aldehyde, and ketone. In one embodiment the nucleophilic group is selected from the group consisting of amine, imine, amide, oxime, thiol, hydroxyl, alkenyl, and carboxyl.

In one embodiment the first reactive functional group is a nucleophilic group and the second reactive functional group is an electrophilic group. In one embodiment the nucleophilic group is selected from the group consisting of amine, imine, amide, oxime, thiol, hydroxyl, alkenyl, and carboxyl. In one embodiment the electrophilic group is selected from the group consisting of epoxy, alkyl halide, ester, aldehyde, and ketone.

In one embodiment the functionalized alkyl silane comprising the first reactive functional group is 3-glycidoxypropyltrimethoxysilane (GPTMS).

In one embodiment the molecule further comprises a third reactive functional group selected from an electrophilic group and a nucleophilic group.

In one embodiment the third reactive functional group is an electrophilic group. In one embodiment the electrophilic group of the third reactive functional group is selected from the group consisting of epoxy, alkyl halide, ester, aldehyde, and ketone.

In one embodiment the third reactive functional group is a nucleophilic group. In one embodiment the nucleophilic group of the third reactive functional group is selected from the group consisting of amine, imine, amide, oxime, thiol, hydroxyl, alkenyl, and carboxyl.

In one embodiment the molecule is a polymer. In one embodiment the polymer is polyethyleneimine (PEI). In one embodiment the polyethyleneimine is a branched polyethyleneimine. In one embodiment the polymer is poly(hexamethylene biguanide).

An aspect of the invention is a method of separation. The method includes the steps of combining a substance of interest, an effective amount of a particle, and a solvent, thereby forming a mixture comprising a complex comprising the substance of interest and the particle; and applying to the mixture a magnetic field of effective strength to influence the mobility of the complex in the mixture. The particle according to this aspect of the invention is a particle comprising a plurality of magnetic nanoparticles, and a silicon oxide shell surrounding the plurality of magnetic nanoparticles, wherein the silicon oxide shell integrally comprises a plurality of functionalized alkyl silanes, wherein each functionalized alkyl silane comprises a reactive functional group selected from the group consisting of an electrophilic group and a nucleophilic group.

In one embodiment the reactive functional group is an electrophilic group. In one embodiment the electrophilic group is selected from the group consisting of epoxy, alkyl halide, ester, aldehyde, and ketone.

In one embodiment the reactive functional group is a nucleophilic group. In one embodiment the nucleophilic group is selected from the group consisting of amine, imine, amide, oxime, thiol; hydroxyl, alkenyl, and carboxyl.

In one embodiment the substance of interest comprises a reactive functional group complementary to the reactive functional group of the particle.

In one embodiment the substance of interest is a toxic pollutant. In one embodiment the toxic pollutant is methylmercury.

In one embodiment the substance of interest is a cell comprising an anionic lipid on its surface. In one embodiment the cell is a bacterium.

An aspect of the invention is a method of separation. The method includes the steps of combining a substance of interest, an effective amount of a particle, and a solvent, thereby forming a mixture comprising a complex comprising the substance of interest and the particle; and applying to the mixture a magnetic field of effective strength to influence the mobility of the complex in the mixture. The particle according to this aspect of the invention is a particle comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

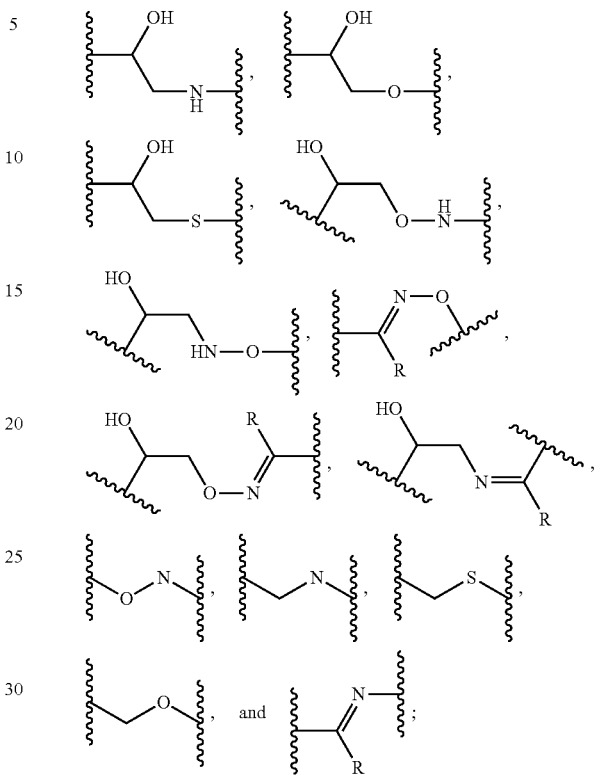

and $FG^3$ is a reactive functional group covalently linked to $L^2$ and selected from the group consisting of an electrophilic group and a nucleophilic group.

In one embodiment $FG^3$ is selected from an electrophilic group and a nucleophilic group, and wherein the substance of interest comprises a reactive functional group complementary to $FG^3$.

In one embodiment $FG^3$ is an electrophilic group. In one embodiment the electrophilic group is selected from the group consisting of epoxy, alkyl halide, ester, aldehyde, and ketone.

In one embodiment $FG^3$ is a nucleophilic group. In one embodiment the nucleophilic group is selected from the group consisting of amine, imine, amide, oxime, thiol, hydroxyl, alkenyl, and carboxyl.

In one embodiment $L^2$-$FG^3$ is a polymer. In one embodiment the polymer is polyethyleneimine (PEI). In one embodiment the polyethyleneimine is a branched polyethyleneimine.

In one embodiment the substance of interest is a toxic pollutant. In one embodiment the toxic pollutant is methylmercury.

In one embodiment the substance of interest is a cell comprising an anionic lipid on its surface. In one embodiment the cell is a bacterium.

An aspect of the invention is a method of killing bacteria. The method includes the step of combining a bacterium, an effective amount of a particle, and a solvent, thereby forming a mixture comprising a complex comprising the bacterium and the particle. The particle according to this aspect of the invention is a particle comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

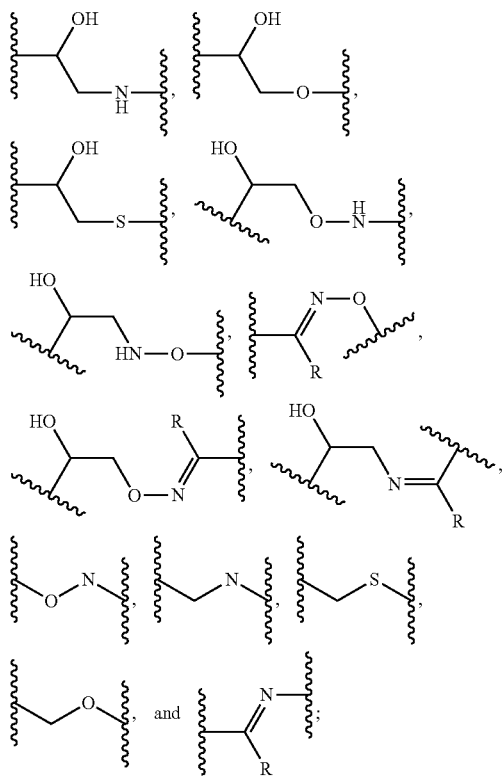

and $FG^3$ is a reactive functional group covalently linked to $L^2$ and selected from the group consisting of an electrophilic group and a nucleophilic group.

In one embodiment $L^2$-$FG^3$ is a polymer. In one embodiment the polymer is poly(hexamethylene biguanide).

In one embodiment the method further includes the step of applying a magnetic field to the solution of effective strength to separate the complex from the solution.

In one embodiment the solution is culture medium.

In one embodiment the solution is water used in aquaculture.

In one embodiment the solution is water used in fish farming.

An aspect of the invention is a separation device, comprising a housing containing a plurality of magnetic particles, wherein the magnetic particles are disposed within the housing so as to permit a fluid within the housing to contact the magnetic particles while retaining essentially all the magnetic particles within the housing.

In one embodiment the magnetic particles are particles each comprising a plurality of magnetic nanoparticles and a silicon oxide shell surrounding the plurality of magnetic nanoparticles, wherein the silicon oxide shell integrally comprises a plurality of functionalized alkyl silanes, wherein each functionalized alkyl silane comprises a reactive functional group selected from an electrophilic group and a nucleophilic group.

In one embodiment the magnetic particles are particles each comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

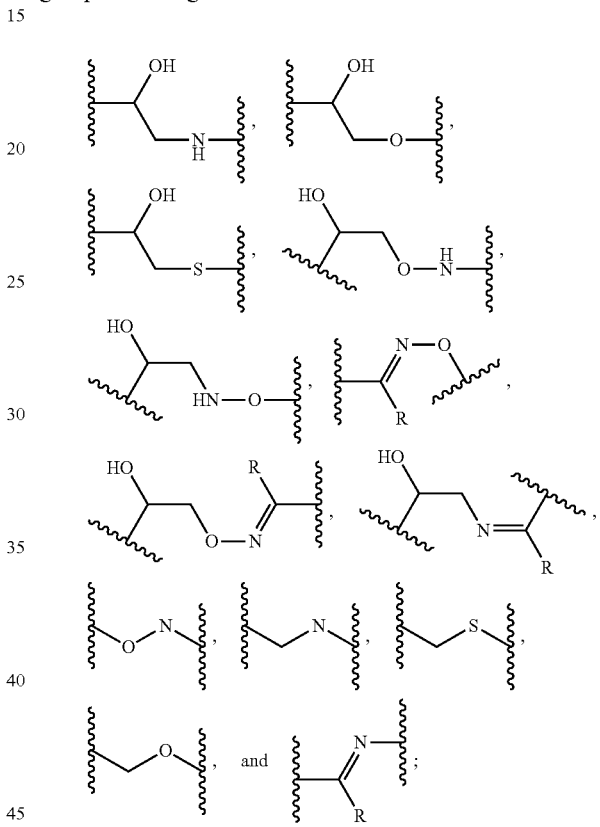

and $FG^3$ is a reactive functional group covalently linked to $L^2$ and selected from an electrophilic group and a nucleophilic group.

In one embodiment the magnetic particles are reversibly disposed on an electromagnetically conductive element such that (i) the magnetic particles are disposed on the conductive element when an electromagnetic current is caused to flow in the conductive element and (ii) the magnetic particles are not disposed on the conductive element when an electromagnetic current is not caused to flow in the conductive element.

In one embodiment the electromagnetically conductive element is a wire.

In one embodiment the fluid within the housing is simultaneously flowing into and out of the housing.

In one embodiment the housing comprises a first opening and a second opening, wherein the first opening and the second opening define ends of a path for passage of the fluid therebetween within the housing.

DETAILED DESCRIPTION OF THE INVENTION

Figure 1:
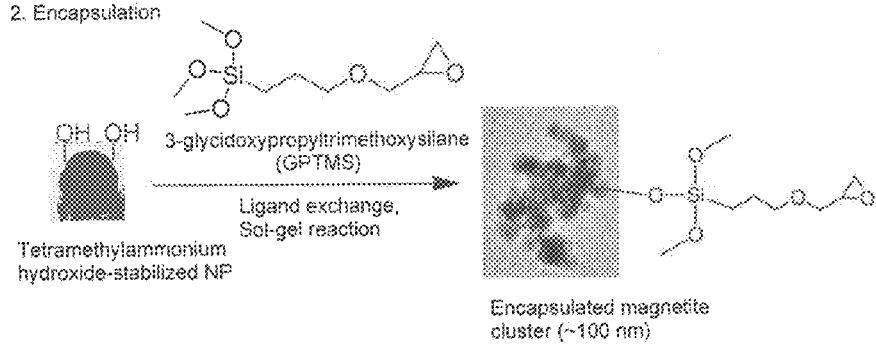
FIG. 1 is a schematic depicting a synthetic route toward thiolated, polyethyleneimine (PEI)-functionalized core-shell magnetite nanoparticles.
Figure 1:
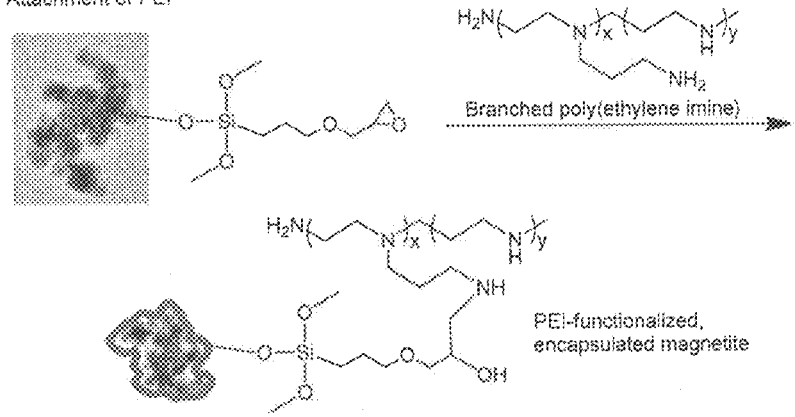
Figure 1:

The invention provides core-shell magnetic particles comprising a magnetic core and a functional shell, methods for making same, methods of separation using same, methods for using same, and devices comprising same. The particles and methods of the invention are useful for targeting and removing substances of interest that may be found in complex mixtures.

A feature of the core-shell magnetic particles of the invention is the incorporation of reactive functional groups directly into the shell of the core-shell magnetic particles. The reactive functional groups are covalently linked to the shell and at least a portion of the reactive functional groups are available on the surface of the shell. The reactive functional groups can be used without further modification, or they may be modified by standard chemical techniques to become alternative reactive functional groups. Additionally, the reactive functional groups can be used to link, via covalent bonds, a plurality of molecules to the core-shell magnetic particles. The molecules so linked to the core-shell magnetic particles can be polymers. In addition, the molecules so linked to the core-shell magnetic particles can themselves include further reactive functional groups which, after the molecules are covalently linked to the core-shell magnetic particles, remain available for interaction with a substance of interest.

In one embodiment the molecules just described specifically exclude antibodies and nucleotides.

The invention concerns core-shell particles. A core-shell particle of the invention is to be understood to refer generally to a core particle essentially completely surrounded by a shell. The core particle generally includes one or more metal particles. The shell generally includes a shell comprising silicon oxide.

The term "particle" as used herein refers to any small subdivision of matter ranging in size from about 0.01 nanometer (nm) to about 1 millimeter (mm) as measured in terms of its greatest diameter. A particle can but need not be spherical in shape, such that it can have a greatest diameter and a least diameter. In one embodiment a particle ranges in size from about 0.01 nm to about 0.1 mm as measured in terms of its greatest diameter. In one embodiment a particle ranges in size from about 0.01 nm to about 0.01 mm as measured in terms of its greatest diameter. In one embodiment a particle ranges in size from about 0.01 nm to about 0.001 mm as measured in terms of its greatest diameter. In one embodiment a particle ranges in size from about 0.01 nm to about 1 micrometer (µm) (i.e., 1000 nm) as measured in terms of its greatest diameter. In one embodiment a particle ranges in size from about 0.01 nm to about 0.1 µm (i.e., 100 nm) as measured in terms of its greatest diameter. In one embodiment a particle ranges in size from about 0.01 nm to about 0.01 micrometer µm (i.e., 10 nm) as measured in terms of its greatest diameter. In one embodiment a particle ranges in size from about 0.1 µm to about 1 µm (i.e., 1000 nm) as measured in terms of its greatest diameter. In one embodiment a particle ranges in size from about 0.1 nm to about 0.1 µm (i.e., 100 nm) as measured in terms of its greatest diameter. In one embodiment a particle ranges in size from about 0.1 nm to about 0.01 µm (i.e., 10 nm) as measured in terms of its greatest diameter. In one embodiment a particle ranges in size from about 1 nm to about 1 µm (i.e., 1000 nm) as measured in terms of its greatest diameter. In one embodiment a particle ranges in size from about 1 nm to about 0.1 µm (i.e., 100 nm) as measured in terms of its greatest diameter. In one embodiment a particle ranges in size from about 1 nm to about 0.01 µm (i.e., 10 nm) as measured in terms of its greatest diameter.

In one embodiment, a particle of the invention is a nanoparticle. As used herein, a "nanoparticle" refers to a particle ranging in size from about 0.1 nm to about 1 µm (i.e., 1000 nm) as measured in terms of its greatest diameter.

The term "nanoparticle" as used herein in one embodiment refers to an uncoated nanoparticle. In another embodiment, the term "nanoparticle" as used herein refers to a coated nanoparticle, e.g., a core-shell nanoparticle of the invention.

As used herein, a particle can include a plurality of subparticles. For example, in one embodiment a particle of the invention can be a cluster of nanoparticles.

As used herein, a nanoparticle can include a plurality of subparticles. For example, in one embodiment a nanoparticle of the invention can be a cluster of smaller particles; a nanoparticle of this type is also referred to herein as a nanocluster.

In reference to a population or plurality of particles, it is to be understood that the term "particle size" is used to refer to a number-average or weight-average particle size as measured by conventional particle size measuring techniques well known to those skilled in the art, such as dynamic or static light-scattering, sedimentation field-flow fractionation, photon-correlation spectroscopy, or disk centrifugation.

Core-shell magnetic particles of the invention are magnetic and thus can be attracted to a magnet and manipulated in or by a magnetic field. The term "magnet" as used herein refers to a substance composed of ferromagnetic or ferrimagnetic material having domains that are aligned to produce a net magnetic field outside the substance or to experience a torque when placed in an external magnetic field. In one embodiment a magnet is an electromagnet. As used herein, an "electromagnet" is a magnet consisting of a coil wound around an iron or steel core, wherein the core is magnetized when an electromagnetic (electric) current flows through the coil.

The term "magnetic field" as used herein refers to a vector field occupying physical space wherein magnetic forces may be detected, typically in the presence of a permanent magnet, current-carrying conductor, or an electromagnetic wave.

The term "magnetic field strength" as used herein refers to a vector field used to describe magnetic phenomena, having the property that the curl of the field is equal to the free current density vector in the meter-kilogram-second system of units.

The term "magnetic nanoparticle" as used herein refers to a coated or uncoated magnetic particle having a particle size of less than or equal to about 1000 nm. In one embodiment, the term "magnetic nanoparticle" refers to a core-shell magnetic particle of the invention having a particle size of less than or equal to about 1000 nm.

The metal in the particles of the present invention may be in the form of a cation belonging to Groups 1-15 of the Periodic Table. These metals include Li, Na, K, Mg, Ca, Sr, Ba, Sc, Y, La, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, and Hg. The term "metal" is also used to include metalloids belonging to groups 13-15. These metalloids include B, Al, Ga, In, Ti, Si, Ge, Sn, Pb, As, Sb, and Bi. In certain embodiments, the metal cations belong to Groups 8-12, which include Fe, Ru, Os, Co, Rh, Ir, Ni, Pd, Pt, Cu, Ag, Au, Zn, Cd, and Hg. In one embodiment, the metal cations of the invention are Fe, Ni, Cu or Zn. In one embodiment, the metal oxides are magnetic metal oxides. Magnetic metal oxides of the invention may include Fe either as Fe(II), Fe(III), or a mixture of Fe(II) and Fe(III). Non-limiting examples of such oxides include FeO, $Fe_2O_3$, and $Fe_3O_4$.

In one embodiment, the core particles are superparamagnetic. In one embodiment, the superparamagnetic core particles comprise magnetite, which in one embodiment, refers to an iron ore that is strongly attracted by a magnet. In one embodiment magnetite has a general formula of $Fe_3O_4$. In one embodiment, the magnetite possesses a $Fe^{2+}$ to $Fe^{3+}$ ratio of about 1:1.5 to about 1:2.5. In one embodiment, the magnetite possesses a $Fe^{2+}$ to $Fe^{3+}$ ratio of about 1:2. In one embodiment, the superparamagnetic particles may comprise chemical equivalents thereof, such as $(Fe,M)OFe_2O_3$ where M may be, in one embodiment, Zn, Co, Ni, Mn, or Cr. In another embodiment, the $Fe^{2+}$ to $Fe^{3+}$ ratio includes any ratio that permits the formation of superparamagnetic nanoparticles in accordance with the method of the present invention.

The term "paramagnetism" as used herein refers to a property exhibited by substances which, when placed in a magnetic field, are magnetized parallel to the field to an extent proportional to the field. The term "paramagnetic" as used herein is used to describe such substances.

The term "superparamagnetism" as used herein refers to the tendency of fine particles to behave independently of one another in a manner similar to paramagnets, so that the particles show a net magnetization in the presence of a magnetic field, but then rapidly relax to show zero net magnetization when the applied magnetic field is removed.

The term "superparamagnetism" is also known in the art as "collective paramagnetism."

Advantage can be taken of the superparamagnetic properties of the core-shell magnetic particles of the invention to separate the particles from their environment following use, allowing multiple uses.

Advantage can also be taken of the superparamagnetic properties of the core-shell magnetic particles of the invention to separate the particles, bound to a substance of interest, from their environment. In so doing, a substance of interest can be separated from its environment.

The core-shell magnetic particles of the invention can be used to effect magnetic separation. The term "magnetic separation" as used herein refers to a process that uses a magnetic solid and an external magnetic field to separate materials or compounds. Examples of magnetic separation include magnetocollection, magnetoflocculation, and magnetoanisotropic sorting.

An aspect of the invention is a particle, comprising a plurality of magnetic nanoparticles and a silicon oxide shell surrounding the plurality of magnetic nanoparticles, wherein the silicon oxide shell integrally comprises a plurality of functionalized alkyl silanes, wherein each functionalized alkyl silane comprises a reactive functional group selected from an electrophilic group and a nucleophilic group.

As used herein, a "functionalized alkyl silane" refers to a bifunctional or polyfunctional chemical compound of the general formula $R-(CH_2)_n-Si-X_m$, wherein R is an organic functional group, Si is a silicon atom, X is OH or a hydrolyzable moiety, n is an integer ranging from 1 to 12, and m is an integer ranging from 1 to 3. In various embodiments X is alkoxy, acyloxy, halogen, or amine. Functionalized alkyl silanes are sometimes referred to in the art as silane coupling agents.

Functionalized alkyl silanes according to the invention specifically include trialkyloxysilanes, monoalkoxysilanes, and dipodal silanes.

In one embodiment R is a nonhydrolyzable organic radical that may possess a functionality that imparts desired characteristics. For example, R may include a reactive functional group selected from an electrophilic group and a nucleophilic group. In one embodiment the reactive functional group is an electrophilic group. In one embodiment the electrophilic group is selected from the group consisting of epoxy, alkyl halide, ester, aldehyde, and ketone. In one embodiment the electrophilic group is epoxy. In one embodiment the reactive functional group is a nucleophilic group. In one embodiment the nucleophilic group is selected from the group consisting of amine, imine, amide, oxime, thiol, hydroxyl, alkenyl, and carboxyl. In one embodiment the nucleophilic group is amine.

Following hydrolysis of X, a reactive silanol group is formed, which can condense with other silanol groups to form siloxane (Si—O) linkages. Stable condensation products are also formed with other oxides such as those of aluminum, zirconium, tin, titanium, nickel, boron, iron, and carbon.

In one embodiment the functionalized alkyl silane comprising the reactive functional group is 3-glycidoxypropyltrimethoxysilane (GPTMS).

The term "alkyl" is art-recognized and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to ten carbons, alternatively from one to about six carbon atoms in its backbone structure. Likewise, "lower alkenyl" and "lower alkynyl" have similar chain lengths.

The term "aralkyl" is art-recognized and includes alkyl groups substituted with an aryl group (e.g., an aromatic or heteroaromatic group).

The terms "alkenyl" and "alkynyl" are art-recognized and include unsaturated aliphatic groups analogous in length and possible substitution to the alkyls described above, but that contain at least one double or triple bond respectively.

The term "heteroatom" is art-recognized and includes an atom of any element other than carbon or hydrogen. Illustrative heteroatoms include boron, nitrogen, oxygen, phosphorus, sulfur and selenium, and alternatively oxygen, nitrogen or sulfur.

The term "aryl" is art-recognized and includes 5-, 6-, and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms "heterocyclyl" and "heterocyclic group" are art-recognized and include 3- to about 10-membered ring structures, such as 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" and "polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and includes an aromatic or non-aromatic ring in which each atom of the ring is carbon. The following art-recognized terms have the following meanings: "nitro" means —$NO_2$; the term "halogen" designates —F, —Cl, —Br, or —I; the term "sulfhydryl" means —SH; the term "hydroxyl" means —OH; and the term "sulfonyl" means —$SO_2^-$.

The terms "amine" and "amino" are art-recognized and include both unsubstituted and substituted amines, e.g., a moiety that may be represented by the general formulas:

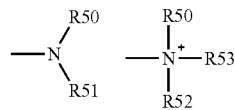

wherein R50, R51 and R52 each independently represent a hydrogen; an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and includes a moiety that may be represented by the general formula:

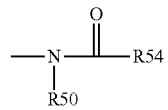

wherein R50 is as defined above, and R54 represents a hydrogen, an alkyl, an alkenyl or —$(CH_2)_m$—R61, where in and R61 are as defined above.

The term "amido" is art-recognized as an amino-substituted carbonyl and includes a moiety that may be represented by the general formula:

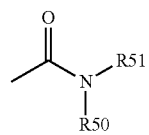

wherein R50 and R51 are as defined above. Certain embodiments of the amide in the present invention will not include imides which may be unstable.

The term "alkylthio" is art-recognized and includes an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art-recognized and includes such moieties as may be represented by the general formulas:

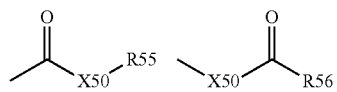

wherein X50 is a bond or represents an oxygen or a sulfur, and R55 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiocarbonyl" group. Where X50 is a sulfur and R55 or R56 is not hydrogen, the formula represents a "thioester." Where X50 is a sulfur and R55 is hydrogen, the formula represents a "thiocarboxylic acid." Where X50 is a sulfur and R56 is hydrogen, the formula represents a "thioformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and include an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The terms "oxime" and "oxime ether" are art-recognized and refer to moieties that may be represented by the general formula:

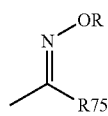

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The term "sulfonate" is art-recognized and includes a moiety that may be represented by the general formula:

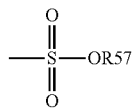

in which R57 is an electron pair, hydrogen, alkyl, cycloalkyl, or aryl.

The term "sulfate" is art-recognized and includes a moiety that may be represented by the general formula:

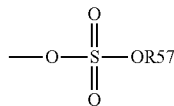

in which R57 is as defined above:

The term "sulfonamido" is art-recognized and includes a moiety that may be represented by the general formula:

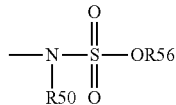

in which R50 and R56 are as defined above.

The term "sulfamoyl" is art-recognized and includes a moiety that may be represented by the general formula:

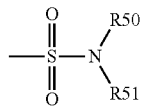

in which R50 and R51 are as defined above.

The term "sulfonyl" is art-recognized and includes a moiety that may be represented by the general formula:

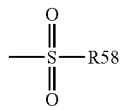

in which R58 is one of the following: hydrogen, alkyl, alkenyl, alkynyl, cycloalkyl, heterocyclyl, aryl or heteroaryl.

The term "sulfoxido" is art-recognized and includes a moiety that may be represented by the general formula:

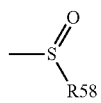

in which R58 is defined above.

The term "phosphoramidite" is art-recognized and includes moieties represented by the general formulas:

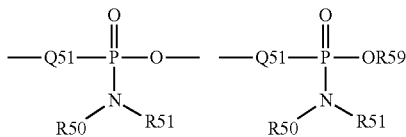

wherein Q51, R50, R51 and R59 are as defined above.

The term "phosphonamidite" is art-recognized and includes moieties represented by the general formulas:

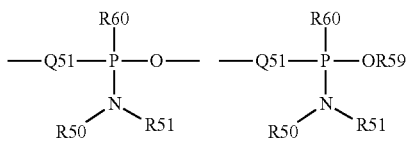

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkynyls, thioalkynyls, carbonyl-substituted alkenyls or alkynyls.

The definition of each expression, e.g. alkyl, m, n, etc., when it occurs more than once in any structure, is intended to be independent of its definition elsewhere in the same structure unless otherwise indicated expressly or by the context.

For purposes of this invention, the chemical elements are identified in accordance with the Periodic Table of the Elements, CAS version, Handbook of Chemistry and Physics, 67th Ed., 1986-87, inside cover.

An aspect of the invention is a particle, comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

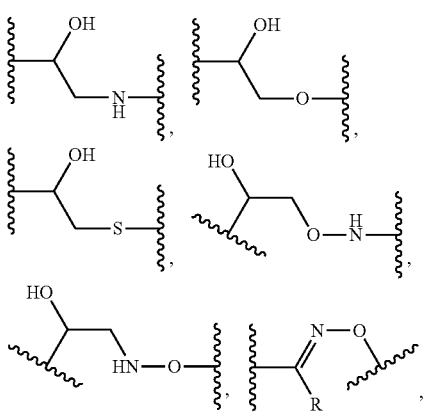

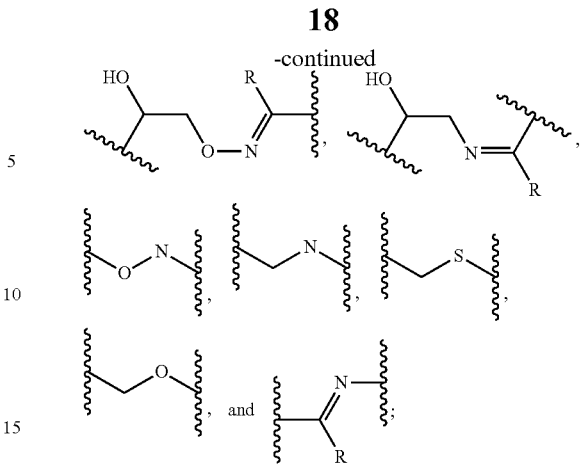

and $FG^3$ is a reactive functional group covalently linked to $L^2$ and selected from an electrophilic group and a nucleophilic group.

The particle (MS) comprising a plurality of magnetic nanoparticles and a silicon oxide shell surrounding the plurality of magnetic nanoparticles is, in one embodiment, a particle such as is disclosed herein, wherein $L^1$ corresponds to a derivative of a reactive functional group associated with a functionalized alkyl silane integrally comprised in the shell.

In one embodiment $L^1$ is a C1-C12 alkyl or alkyloxy.

In one embodiment $L^2$ is a C1-C12 alkyl or alkyloxy.

In one embodiment X represents a covalent linkage arising from reaction of an electrophilic group with a suitable complementary nucleophilic group. In one embodiment the electrophilic group is as disclosed above. In one embodiment the nucleophilic group is as disclosed above. In one embodiment the electrophilic group and nucleophilic group are as disclosed above.

In one embodiment $FG^3$ is an electrophilic group as disclosed above. In one embodiment $FG^3$ is a nucleophilic group as disclosed above.

In one embodiment $L^2$-$FG^3$ represents a straight or branched polymer comprising at least one reactive functional group $FG^3$ that is available to interact with another molecule. Alternatively, $FG^3$ of the polymer can be derivatized, using standard chemical methods, to become a different reactive functional group.

In one embodiment $L^2$-$FG^3$ represents polyethyleneimine (PEI), which includes reactive functional groups in the form of primary, secondary, and tertiary amines. In one embodiment the polyethyleneimine is a branched polyethyleneimine.

In one embodiment the polymer is poly(hexamethylene biguanide), which includes imines and secondary amines.

An aspect of the invention is a method for producing a core-shell magnetic particle of the invention. The method includes the step of combining (i) an aqueous solution of magnetic nanoparticles with (ii) a reactive silicate and (iii) a functionalized alkyl silane comprising a reactive functional group selected from an electrophilic group and a nucleophilic group, under conditions permitting formation of the silicon oxide shell surrounding the magnetic nanoparticles and integrally comprising the functionalized alkyl silane. As described in the Examples below, the method can involve a simple aqueous co-precipitation of iron chloride salts, producing aggregates small polydisperse magnetite nanoparticles. These polydisperse magnetite nanoparticles can be rendered soluble in aqueous solution such that they remain in solution. In one embodiment this is accomplished with the introduction of tetramethylammonium hydroxide into the aqueous solution.

An alternative method involves thermal decomposition of iron tri(acetylacetonate) followed by emulsion droplet solvent evaporation to form well-defined spherical clusters of monodisperse magnetite nanoparticles. Both methods produce magnetic cores generally on the order of 100 nm in size.

As used herein, a "reactive silicate" refers to a form of silica that is slightly ionized and has not been incorporated into a polymer. In one embodiment a reactive silicate is tetraethoxysilane (TEOS). In one embodiment a reactive silicate is aminopropyltrimethoxysilane (APTS).

In one embodiment the functionalized alkyl silane comprising the reactive functional group is 3-glycidoxypropyltrimethoxysilane (GPTMS).

An aspect of the invention is a method for producing a core-shell magnetic particle of the invention. The method includes the steps of combining (i) an aqueous solution of magnetic nanoparticles with (ii) a reactive silicate and (iii) a functionalized alkyl silane comprising a first reactive functional group selected from an electrophilic group or a nucleophilic group, under conditions permitting the formation of the silicon oxide shell surrounding the magnetic nanoparticles and integrally comprising the functionalized alkyl silane; and linking the functionalized alkyl silane to a molecule through a covalent bond formed by reaction of the first reactive functional group with a second reactive functional group of the molecule, wherein the second reactive functional group (i) is complementary to the first reactive functional group and (ii) is selected from an electrophilic group and a nucleophilic group. This method can be used, for example, to prepare a particle in accordance with the representation $(MS)-L^1-X-L^2-FG^3$, discussed above.

In one embodiment $FG^3$ is an electrophilic group as disclosed above. In one embodiment $FG^3$ is a nucleophilic group as disclosed above.

In one embodiment $L^2-FG^3$ represents a straight or branched polymer comprising at least one reactive functional group $FG^3$ that is available to interact with another molecule. Alternatively, $FG^3$ of the polymer can be derivatized, using standard chemical methods, to become a different reactive functional group.

In one embodiment $L^2-FG^3$ represents polyethyleneimine, which includes reactive functional groups in the form of primary, secondary, and tertiary amines. In one embodiment the polyethyleneimine is a branched polyethyleneimine.

In one embodiment the polymer is poly(hexamethylene biguanide), which includes imines and secondary amines.

In one embodiment the functionalized alkyl silane comprising the reactive functional group is 3-glycidoxypropyltrimethoxysilane (GPTMS).

An aspect of the invention is a method of separation. The method includes the steps of combining a substance of interest with an effective amount of a particle in a solution under conditions that allow the substance of interest and the particle to form a complex; and applying a magnetic field to the solution of effective strength to separate the complex from the solution. The particle according to this aspect of the invention is a particle comprising a plurality of magnetic nanoparticles and a silicon oxide shell surrounding the plurality of magnetic nanoparticles, wherein the silicon oxide shell integrally comprises a plurality of functionalized alkyl silanes, wherein each functionalized alkyl silane comprises a reactive functional group selected from an electrophilic group and a nucleophilic group.

As used herein, a "substance of interest" refers to a compound or composition of matter that is a subject of interest to isolate or target. A substance of interest can include metals, inorganic molecules, organic molecules, biomolecules, viruses, components of viruses, cells, cellular organelles, other cellular components, toxins, and toxic pollutants. Inorganic molecules can include organometallic compounds, such as methylmercury. Organic molecules of interest specifically can include metalloproteins. Biomolecules specifically can include, without limitation, nucleic acids, peptides, proteins, carbohydrates, lipids, hormones, and any combination thereof.

Cells of interest can include prokaryotic cells and eukaryotic cells. In one embodiment a cell is a bacterium. In one embodiment a cell is a yeast cell. In one embodiment a cell is a mammalian cell. In one embodiment a cell is a human cell. In one embodiment a cell is a sperm cell. In one embodiment a cell is an oocyte. In one embodiment a cell is a stem cell. In one embodiment a cell is a cancer cell.

As used herein, a "toxic pollutant" refers to any metal, metal-containing compound, inorganic molecule, or organic molecule that is present in the environment and is toxic to cells. In one embodiment a toxic pollutant is a toxic pollutant that is introduced into the environment as a result of human activity, e.g., manufacturing or processing. In one embodiment a toxic pollutant is present in water. In one embodiment a toxic pollutant is present in soil. In one embodiment a toxic pollutant is methylmercury.

Methylmercury (sometimes methylmercury) is an organometallic cation with the formula $[CH_3Hg]^+$. It is a bioaccumulative environmental toxicant. In the past, methylmercury was produced directly and indirectly as part of several industrial processes such as the manufacture of acetaldehyde. Currently there are few human-origin sources of methylmercury pollution other than as an indirect consequence of the burning of wastes containing inorganic mercury and from the burning of fossil fuels, particularly coal. Although inorganic mercury is only a trace constituent of such fuels, their large scale combustion in the United States alone results in release of some 80.2 tons of elemental mercury to the atmosphere each year, out of total anthropogenic emissions in the United States of 158 tons. Natural sources of mercury to the atmosphere include volcanoes, forest fires, and weathering of mercury-bearing rocks.

Methylmercury is formed from inorganic mercury by the action of anaerobic organisms that live in aquatic systems including lakes, rivers, wetlands, sediments, soils, and the open ocean. This methylation process converts inorganic mercury to methylmercury in the natural environment. Acute methylmercury poisoning occurred at Grassy Narrows in Ontario, Canada as a result of mercury released from the mercury-cell chloralkali process, which uses liquid mercury as an electrode in a process that entails electrolytic decomposition of brine, followed by mercury methylation in the aquatic environment.

An acute methylmercury poisoning tragedy occurred in Minamata, Japan following release of methylmercury into Minamata Bay and its tributaries. In the Ontario case, inorganic mercury discharged into the environment was methylated in the environment; whereas in Minimata, Japan, there was direct industrial discharge of methylmercury.

Because methylmercury is formed in aquatic systems and because it is not readily eliminated from organisms, it is biomagnified in aquatic food chains from bacteria, to plankton, through microinvertebrates, to herbivorous fish, and to piscivorous (fish-eating) fish. At each step in the food chain, the concentration of methylmercury in the organism increases. The concentration of methylmercury in the top level aquatic predators can reach a level a million times higher than the level in the water. This is because methylmercury has a half-life of about 72 days in aquatic organisms, resulting in its bioaccumulation within these food chains. Organisms, including humans, fish-eating birds, and fish-eating mammals such as otters and whales that consume fish from the top of the aquatic food chain receive the methylmercury that has accumulated through this process. Fish and other aquatic species are the only significant source of human methylmercury exposure.

The concentration of mercury in any given fish depends on the species of fish, the age and size of the fish and the type of water body in which it is found. In general, fish-eating fish such as shark, swordfish, marlin, larger species of tuna, walleye, largemouth bass, and northern pike have higher levels of methylmercury than herbivorous fish or smaller fish such as tilapia and herring. Within a given species of fish, older and larger fish have higher levels of methylmercury than smaller fish. Fish that develop in water bodies that are more acidic also tend to have higher levels of methylmercury.

In humans, ingested methylmercury is readily and completely absorbed by the gastrointestinal tract. It is mostly found complexed with free cysteine and with proteins and peptides containing that amino acid. The methylmercuric-cysteinyl complex is recognized by amino acid transporting proteins in the body as methionine, another essential amino acid. Because of this mimicry, it is transported freely throughout the body including across the blood-brain barrier and across the placenta, where it is absorbed by the developine fetus. Also for this reason as well as its strong binding to proteins, methylmercury is not readily eliminated. Methylmercury has a half-life in human blood of about 50 days.

In one embodiment, use of the core-shell magnetic particles for cell separations may be accomplished, as follows: a mixed population of cells obtained from any of various body fluids, such as bone marrow, blood, urine, sputum or secretion is obtained, using standard procedures. The core-shell magnetic particles may be directly functionalized with one or more functional groups capable of binding to a molecule expressed on the cell surface of the cell of interest. After binding of the functionalized core-shell magnetic particles to the target cells of interest is allowed to occur, magnetic separation of the magnetic particles from the suspension is performed. A similar scheme may be employed for a protein of interest, or nucleic acid of interest, for isolation from a biological sample, a culture to medium, a bacterial or yeast culture, and many other scenarios, as will be apparent to one skilled in the art.

In one embodiment, the core-shell magnetic particles of the invention are used for enrichment of a particular cell population, which differs in terms of cell size, membrane charge, etc., which is present in a mixed population. In one embodiment, the population of interest shows greater binding affinity for the core-shell magnetic particles of the invention, as compared to other cell populations, and the population of interest is removed and then dissociated from the particles. In another embodiment, the population of interest exhibits lower affinity for the core-shell magnetic particles, as compared to other cell populations, the removal of the latter of which is accomplished via contact with the core-shell magnetic particles. It is to be understood that any use of core-shell magnetic particles of the invention for the purpose of enriching cell populations or separations is to be considered as part of this invention.

In one embodiment, the magnetic separation of the complex is via high gradient magnetic separation. In one embodiment, the method is utilized to separate a protein expressed by a cell from said cell. In one embodiment, the protein is strongly cationic.

In another embodiment, the method of this invention is conducted in a solution or broth. In another embodiment, the cell is a bacterium or yeast cell.

According to this aspect of the invention, and in one embodiment, magnetic separation of the complex is via high gradient magnetic separation. In one embodiment, the core-shell magnetic particle has a size of from 20-1000 nm. In another embodiment, the solution of high ionic strength ranges in concentration from 0.1 M to 0.4 M. In another embodiment, the concentration of core-shell magnetic particle in solution ranges from 0.05% to 0.3%.

In one embodiment, the cell is a bacterium or a yeast cell. In one embodiment, it is desirable to separate prokaryotic or eukaryotic cells in a culture system or broth, or in another embodiment, it is desirable to isolate a protein expressed in a culture comprising prokaryotic or eukaryotic cells. In one embodiment, the prokaryotic or eukaryotic cells may be engineered to express a heterologous protein, which, in one embodiment, is desirable to separate from bacteria or eukaryotic cells expressing the protein.

In another embodiment, the method of this invention is conducted in a solution or broth, which may, in another embodiment, be any such solution or broth, suitable for the particular substance being isolated, and the environment the substance is being isolated from, as will be appreciated by one skilled in the art.

For example, and in one embodiment, appropriate conditions for isolating proteins expressed by bacteria in culture or broth may be found in Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y.

In another embodiment, the proteins of interest may be expressed in mammalian cells, which may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. In addition, any of the media described in Ham et al. (1979) Meth. Enzymol. 58:44; Barnes et al. (1980) Anal. Biochem. 102:255; U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the mammalian cells.

In one embodiment, the protein being separated is secreted from the cell expressing the same. In one embodiment, the protein is expressed intracellularly.

In one embodiment, the cell expressing the protein, or in another embodiment, the cell comprising a virus which is genetically engineered to produce the protein, is lysed, by means as will be known to one skilled in the art, such as, for example, via the use of detergent or osmotic shock.

In one embodiment, the protein is separated via the methods of this invention, as described. In another embodiment, the culture medium, or in another embodiment, cell lysate, or in another embodiment, tissue/organ homogenate is centrifuged to remove particulate cell debris, and the solution, lysate, homogenate, etc., is fractionated on an ion-exchange column, and/or in another embodiment, chromatography on silica or on a cation-exchange resin such as DEAF; and/or in another embodiment, gel filtration, following which, magnetic separation according to the methods of this invention are performed. In one embodiment, the protein is not particularly cationic, and the methods employed are in order to diminish contaminating virus present in the protein preparation.

In another embodiment, a protease inhibitor, such as phenyl methyl sulfonyl fluoride (PMSF), may be used in the methods of this invention, in order to inhibit proteolytic degradation during purification.

In one embodiment, the methods of this invention are useful in removing viruses, which are too small to be removed by traditional filtration or centrifugation, from a culture, thereby obviating the need for ultrafiltration, which carries a large expense in terms of protein recovery, or the need for viral inactivation by acids or detergents, which may affect protein activity.

An aspect of the invention is a method of separation. The method includes the steps of combining a substance of interest with an effective amount of a particle in a solution under conditions that allow the substance of interest and the particle to form a complex; and applying a magnetic field to the solution of effective strength to separate the complex from the solution. The particle according to this aspect of the invention is a particle comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

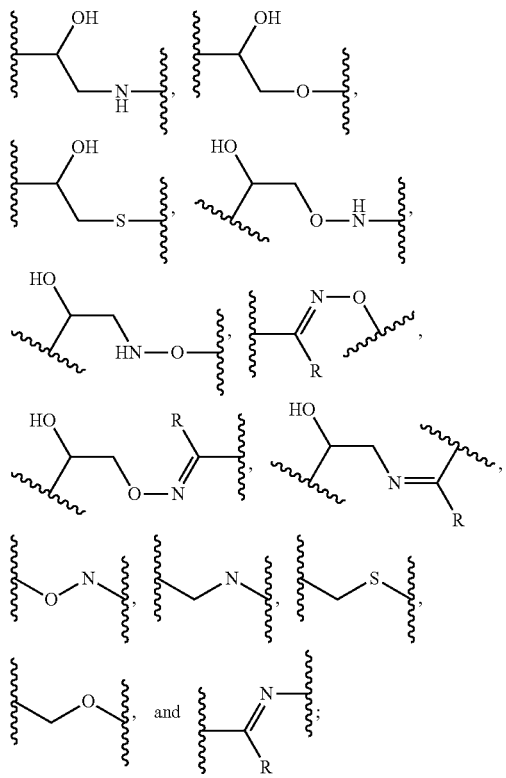

and $FG^3$ is a reactive functional group covalently linked to $L^2$ and selected from an electrophilic group and a nucleophilic group.

An aspect of the invention is a method of killing bacteria. The method includes the step of combining a bacterium of interest with an effective amount of a particle in a solution under conditions that allow the bacterium of interest to form a complex with the particle. The particle according to this aspect of the invention is a particle comprising (MS)-$L^1$-X-$L^2$-$FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

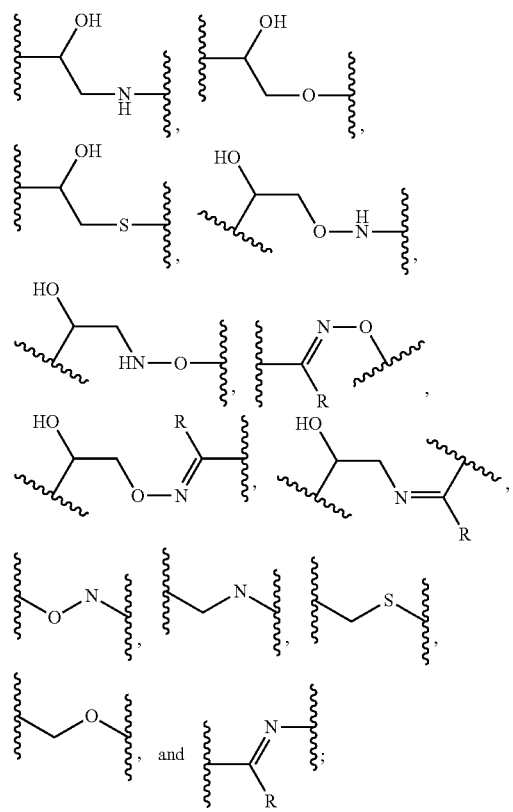

and $FG^3$ is a reactive functional group covalently linked to $L^2$ and selected from an electrophilic group and a nucleophilic group.

In one embodiment $L^2$-$FG^3$ is a polymer. In one embodiment the polymer is poly(hexamethylene biguanide).

In one embodiment the method further includes the step of applying a magnetic field to the solution of effective strength to separate the complex from the solution.

In one embodiment the solution is culture medium.

In one embodiment the solution is water used in aquaculture.

In one embodiment the solution is water used in fish farming.

An aspect of the invention is a separation device, comprising a housing containing a plurality of magnetic particles, wherein the magnetic particles are disposed within the housing so as to permit a fluid within the housing to contact the magnetic particles while retaining essentially all the magnetic particles within the housing.

In one embodiment the magnetic particles are particles each comprising a plurality of magnetic nanoparticles and a silicon oxide shell surrounding the plurality of magnetic nanoparticles, wherein the silicon oxide-shell integrally comprises a plurality of functionalized alkyl silanes, wherein each functionalized alkyl silane comprises a reactive functional group selected from an electrophilic group and a nucleophilic group.

In one embodiment the magnetic particles are particles each comprising $(MS)-L^1-X-L^2-FG^3$, wherein (MS) is a particle comprising a plurality of magnetic nanoparticles and a silicon oxide shell surrounding the plurality of magnetic nanoparticles;

$L^1$ is an alkyl or alkyloxy linker moiety integral to the silicon oxide shell;

$L^2$ is an alkyl or alkyloxy linker moiety;

X is a covalent linkage joining $L^1$ and $L^2$, selected from the group consisting of

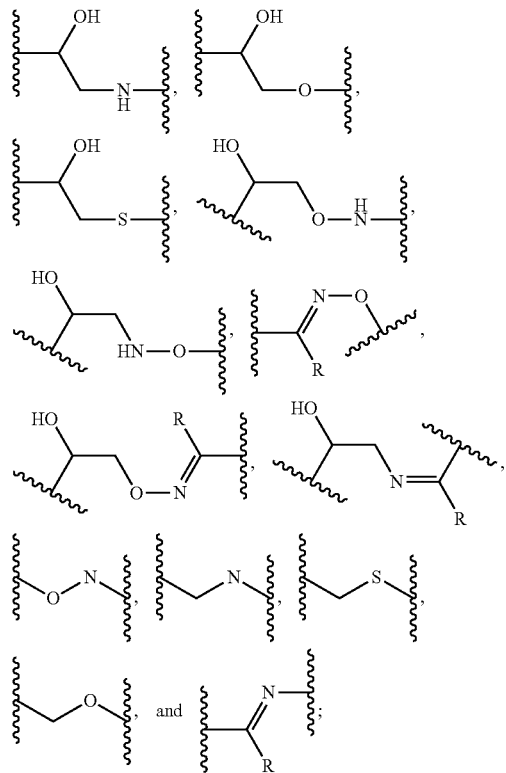

and $FG^3$ is a reactive functional group covalently linked to $L^2$ and selected from an electrophilic group and a nucleophilic group.

In one embodiment the magnetic particles are reversibly disposed on an electromagnetically conductive element such that (i) the magnetic particles are disposed on the conductive element when an electromagnetic current is caused to flow in the conductive element and (ii) the magnetic particles are not disposed on the conductive element when an electromagnetic current is not caused to flow in the conductive element.

In one embodiment the electromagnetically conductive element is a wire.

In one embodiment the fluid within the housing is simultaneously flowing into and out of the housing.

The device can be constructed and arranged for use in a static or dynamic fashion with respect to the fluid, that is, with fluid that is static within the housing or moving within or through the housing. For example, in one embodiment fluid is introduced into the housing and allowed to stand for a period sufficient to permit interaction between a substance of interest in the fluid and the magnetic particles present within the housing; the fluid is then removed, leaving behind magnetic particles complexed with the substance of interest. Alternatively, the fluid can be introduced into the housing and then stirred but not replenished during the period of interaction.

In one embodiment fluid is being introduced into and removed from the housing simultaneously, such that the device forms part of a flow path for the fluid.

In one embodiment the housing comprises a first opening and a second opening, wherein the first opening and the second opening define ends of a path for passage of the fluid therebetween within the housing. One or both openings may be fitted to reversibly attach to a fluid path or circuit, e.g., with hose connectors or Luer fittings.

The core-shell magnetic particles of the invention may be in a composition that is biocompatible. In one embodiment, core-shell magnetic particles can be mixed with a suitable pharmaceutically acceptable carrier or excipient, such as disclosed in Remington's Pharmaceutical Sciences, Mack Publishing Company, Easton, Pa., USA, 1985. The particles may be used in the treatment or diagnosis of certain conditions such as in tagging, detecting and/or removing cancer cells for example from a sample or tissue. In one embodiment, the core-shell magnetic particles of the invention can be utilized in the detoxification of, and/or recovery of a desired substance from, domestic and industrial wastes.

In one embodiment, this invention provides a solution comprising a core-shell magnetic particle which is an aqueous solution. In one embodiment, this invention provides a solution comprising a core-shell magnetic particle which is an aqueous solution of high ionic strength.

In one embodiment, the magnetic properties of the core-shell magnetic particles of the invention are such that the particles exhibit magnetic behavior only when in a magnetic field gradient, and do not become permanently magnetized.

EXAMPLES

The invention now being generally described, it will be more readily understood by reference to the following examples, which are included merely for purposes of illustration of certain aspects and embodiments of the present invention, and are not intended to limit the invention.

Example 1

Synthesis and Characterization of Core-Shell Magnetic Nanoparticles Functionalized with Thiol Groups Particle Synthesis The synthetic route applied to obtain the encapsulated particles herein resulted from numerous optimization efforts and consists of three essential steps as shown in FIG. 1.

1. Magnetite Stabilized by Tetramethylammonium Hydroxide (TMAOH).

An aqueous solution of $FeCl_3.6H_2O$ (7.58 g, 28 mmol) and $FeCl_2.4H_2O$ (2.78 g, 14 mmol) was brought to 80° C. under continuous nitrogen purge within approximately 20 min. The solution was poured into 25 mL of 30% aqueous solution of NH$_4$OH and the ensued precipitate was stirred and kept in a sealed reactor at 80° C. for 1 h. The resulting particle suspension was sonicated for 1 min and particles were separated by magnetocollection and suspended in 30 mL of 0.33 M tetramethylammonium hydroxide. The suspension was observed to be stable. The above steps were repeated three times and the resulting fractions were combined to obtain a stable suspension of magnetite particles (100 mL).

Tetramethylammonium hydroxide adsorbs onto the surface of magnetite and acts as a charge stabilizer for the particles to remain suspended in water rather than sediment out of suspension in the form of large aggregates. The density of magnetite is 4.5 g/cm$^3$ and the particles would aggregate and precipitate if they were not colloidally stabilized.

2. Magnetite Encapsulated by PEI-Functionalized Silica Shell (PEI-M/SiO$_2$).

To the suspension above, 100 mL of absolute ethanol were added and the diluted suspension was sonicated for 1 min. Then tetraethoxysilane (TEOS, 10 g, 48 mmol) was added followed by sonication for 5 min and addition of 3-glycidoxypropyl trimethoxysilane (GPTMS, 11.3 g, 48 mmol). The resulting suspension was shaken (200 rpm) at room temperature for 1 h and aqueous solution of branched poly(ethylene imine) (PEI, solution of 23.5 g BASF Lupasol® G20, MW 1300 in 100 mL water) was added and the resulting mixture was shaken at room temperature for 1 h, kept at 80° C. for 1 h and then shaken at room temperature for 16 h. The suspension was then dialyzed against excess deionized water (membrane molecular weight cut-off (MWCO), 12-14 kDa). The resulting suspension did not exhibit any visible sedimentation of particles for several days at rest.

TEOS was allowed to start forming the shell around magnetite, which was not fully cured yet (typical 100% reaction times, 16-24 h and not 5 min) and still capable of reacting with GPTMS, which was added shortly later. In this way, GPTMS was introduced while the shell was forming, rather than after formation of the shell was already essentially complete.

The GPTMS was incorporated into the surface of the growing silica shell, in accordance with classical sol-gel chemistry. As a result, there are multiple points for attachment of GPTMS onto silica as well as residual —OH groups on the magnetite surface.

Approximately 50% of the suspension was snap-frozen and lyophilized for further modification.

3. Thiolated PEI-Functionalized Silica Shell Particles (SH-PEI-M/SiO$_2$).

PEI-M/SiO$_2$ particles from the above synthesis were thiolated by ethylene sulfide as follows. Dry particles (50 mg) were suspended in absolute ethanol (10 mL) with sonication. Ethylene sulfide (100 μL, 1.66 mmol) was added, the suspension was shaken at room temperature for 24 h, and ethanol was evaporated under vacuum. An identical synthesis was repeated in deionized water, for comparison purposes. The resulting samples were redispersed in deionized water with brief sonication and purified by dialysis (MWCO, 12-14 kDa).

Particle Characterization

Figure 2:
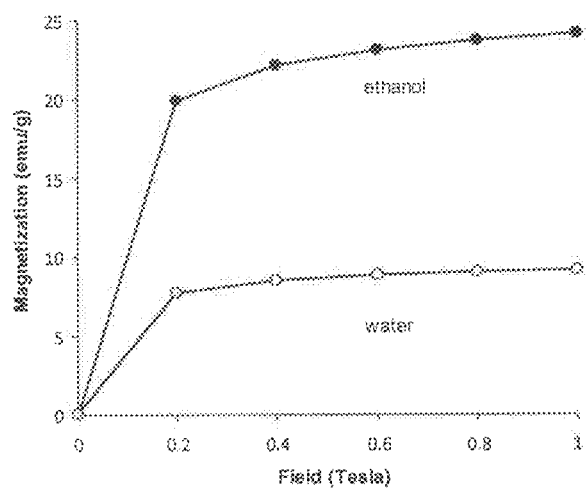
FIG. 2 depicts superconducting quantum interference device (SQUID) magnetization-field data for thiolated PEI-functionalized core-shell magnetite nanoparticles (SH-PEI-M/SiO$_2$ particles) synthesized in ethanol and water.
Figure 3:
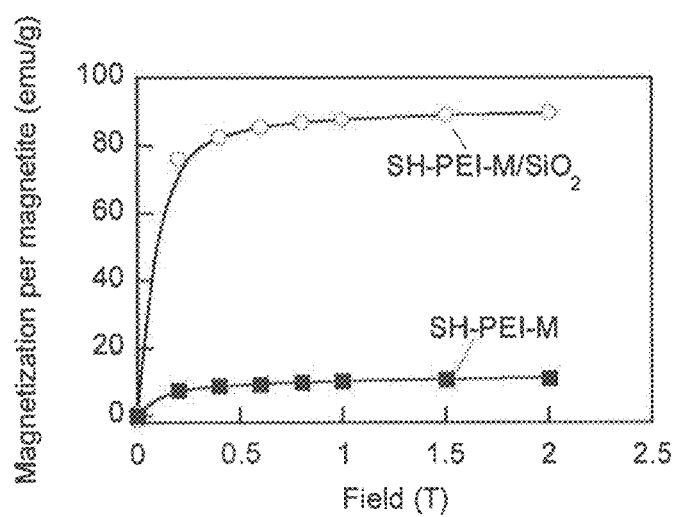
FIG. 3 depicts SQUID magnetization-field data for SH-PEI-M/SiO$_2$ and non-encapsulated SH-PEI-M particles. Magnetization is given per magnetite content.
Figure 4:
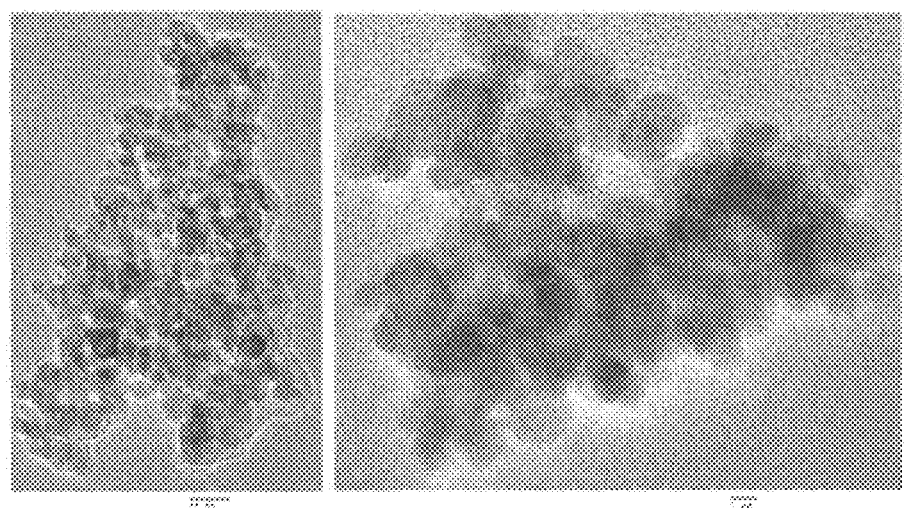
FIG. 4 depicts typical high resolution transmission electron microscopy (HRTEM) images of PEI-M/SiO$_2$ particles of the invention. Bar sizes shown are 20 nm (left) and 5 nm (right).

The resulting particles were characterized by elemental analysis, transmission electron microscopy (TEM), thermogravimetric analysis (TGA), superconducting quantum interference device (SQUID), and zeta (ζ)-potential measurements. In elemental analysis measurements (performed using an Agilent 7500a Series ICP-MS), the experimental composition and TGA data were reconciled with computed structures. It appeared that thiolation in water resulted in at least 2-fold lower saturation magnetization (FIG. 2), and hence, particles thiolated in ethanol were further studied. Herein, particles were suspended in deionized water at 1 mg/mL concentration and kept at room temperature and in the presence of oxygen for 1 week. The suspensions were then snap-frozen, lyophilized and subjected to SQUID analysis. It should be noted that thiolated core-shell particles synthesized as described above in ethanol were characterized by very high saturation magnetization (84-92 emu/g of magnetite) and were substantially more stable, magnetization-wise, than their non-encapsulated counterparts synthesized as previously described and then thiolated (FIG. 3): Note that the saturation magnetization of SH-PEI-M/SiO$_2$ is close to that of freshly prepared bare magnetite (91-92 emu/g). Judging by HRTEM (FIG. 4), the particles were 6-10 nm primary magnetite particles encapsulated by TEOS/GPTMS to form ~100 nm clusters of irregular shape.

Example 2

Remediation Processes Using Core-Shell Magnetic Nanoparticles Described in Example 1

Magnetic Separation-Assisted Removal of Methylmercury Chloride from Water

Stock solutions of methylmercury chloride (MeHg) were prepared by dissolving approximately 100 mg of MeHg in deionized water. Dissolution resulting in a transparent solution occurred within approximately 7 to 10 days at room temperature with periodic shaking. The stock solution was diluted accordingly to result in either 82 ppm (mg/L) or 9640 ppb (μg/L) initial concentrations. Thoroughly measured aliquots of 7 mg/mL suspension of thiolated core-shell nanoparticles according to Example 1 were placed in tubes followed by lyophilization of the suspensions in the same tubes. Then 40 mL of MeHg stock solution was added into each tube, the tubes were briefly sonicated to resuspend nanoparticles, and the resulting suspensions were shaken at 200 rpm for 10 days at room temperature, to ensure equilibrium uptake of MeHg. The magnetic particles were then held to the bottom of the tubes by a 1.2 T magnet and the supernatant was carefully separated and subjected to an atomic absorption (AA) spectroscopy analysis for mercury using a Cetac M6000A Automated Mercury Analyzer (CETAC Technologies, Omaha, Neb.). The AA measurements were conducted in duplicate.

Figure 5:
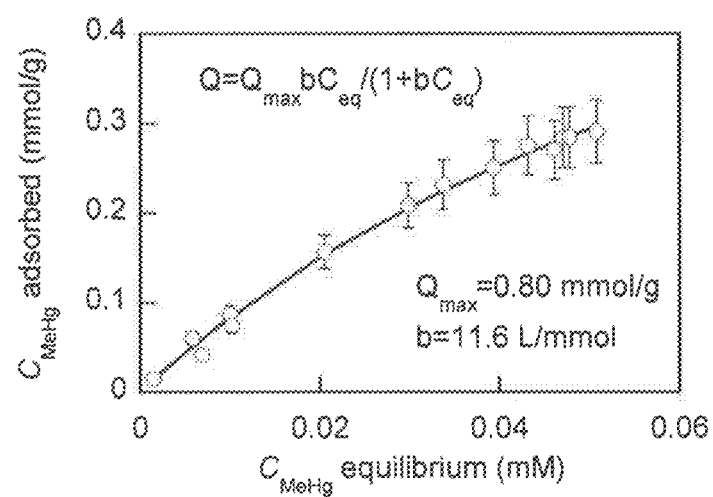
FIG. 5 depicts adsorption isotherm of methylmercury onto thiolated magnetite nanoparticles. Solid line indicates the fit to Langmuir adsorption isotherm and is shown to guide the eye only.
Figure 6:
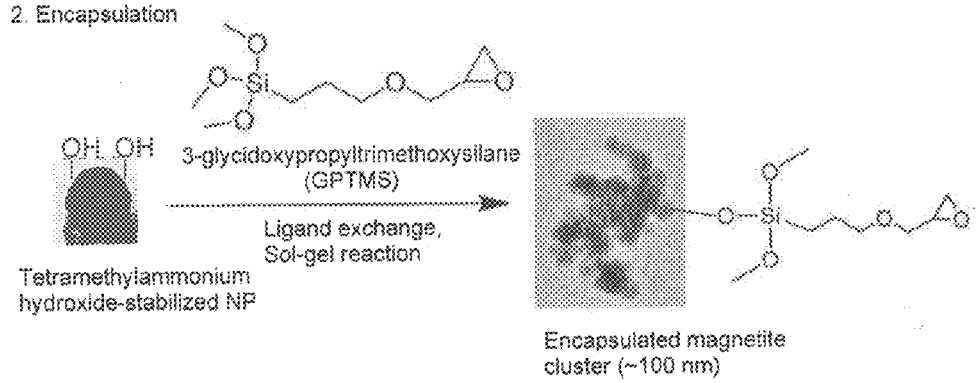
FIG. 6 is a schematic depiction of the synthesis of poly (hexamethylene biguanide) (PHMBG)-M/SiO$_2$ particles.
Figure 6:
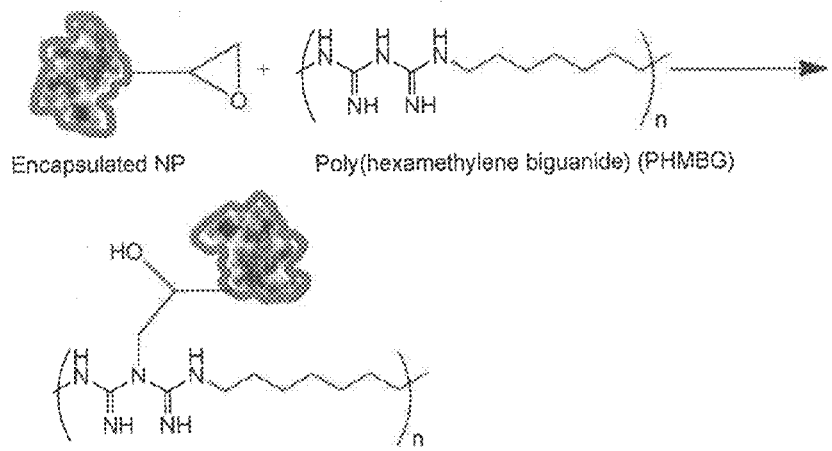

Results of the MeHg adsorption measurements are shown in FIG. 5. The to supernatant separated from particles contained less than 0.1 ppm of iron, indicating that the particles were efficiently removed from the suspension. The pH 4.6 was measured to be in all samples.

In a control experiment, 1 mg/mL suspension of non-thiolated PEI-M/SiO$_2$ particles was tested for MeHg removal from 9.64 ppm stock solution. No change in mercury concentration was observed upon equilibration with non-thiolated particles.

Figure 7:
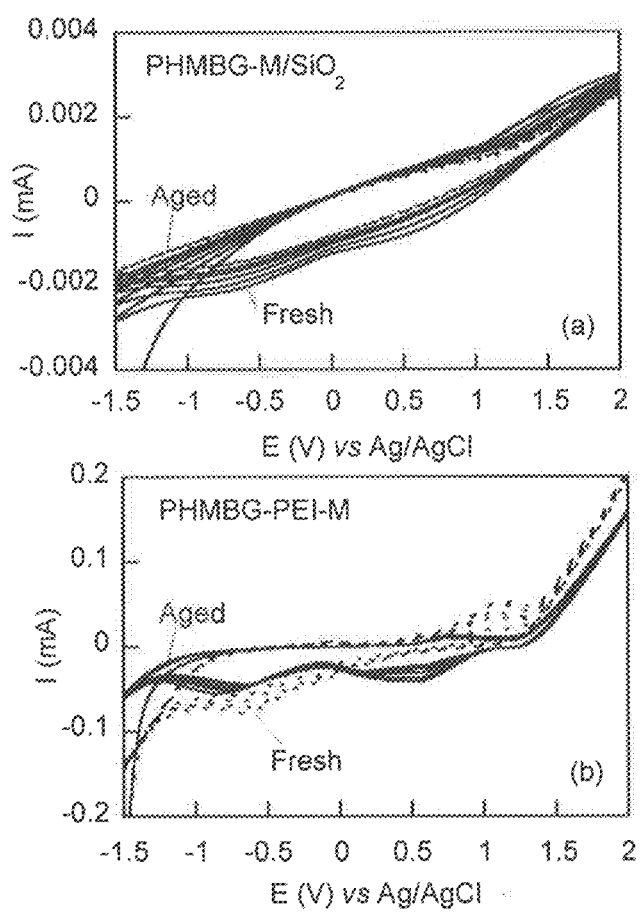
FIG. 7 depicts cyclic voltammetry of (a) PHMBG-M/SiO$_2$ and (b) PHMBG-PEI-M particles in 0.1 M HCl. Fresh and aged samples are shown by solid and dotted lines, respectively.

Without being bound by any theory, the shape of the adsorption isotherm resembled that of Langmuir isotherms, which can be expressed as:

$$Q = Q_{max} \frac{bC_e}{1 + bC_e},$$

where Q is the amount (in mmol/g) of MeHg adsorbed per gram of particles, b is the equilibrium constant in L/mmol, and $C_e$ is the concentration of MeHg in the solution equilibrated with the particles in mM. Thus, values were fitted for $Q_{max}$ and b using Matlab, and the results are presented in FIG. 7. With a percent error of 6.58%, the values were determined to be $Q_{max}$=0.8 mmol/g and b=11.6 L/mmol.

Elemental analysis indicated that there was one mole of thiol (SH) groups per 2491 grams of nanoparticles, or 2.0 mmol/g. Thus, there were 0.4 moles of methylmercury adsorbed per mole of SH groups, or one molecule of methylmercury was adsorbed per 2.5 molecules of SH groups on the nanoparticle shell. This may be explained by some steric hindrances of the thiol groups that are close to the particle surfaces. In addition, the SH-PEI-SiO$_2$-M particles are positively charged at pH 4.6 (observed ζ-potential, 25.7±1.65 mV) and hence can repulse the cationic $CH_3Hg^+$ species.

The thiolation of the particles is a simple process that can be modified to produce particles with a varied and high payload of thiol groups. Such thiolation does not diminish the paramagnetic properties of the particles, which are protected by the silica encapsulation. The particles are readily removed from water by magnetic separation and thereby enable efficient removal of methylmercury. Methylmercury concentrations in the environment below 10 ppb levels can be achieved using these nanoparticles, as required by the United States EPA Clean Water Act.

Example 3

Synthesis of Core-Shell Magnetic Nanoparticles Modified with Biguanide

Poly(hexamethylene biguanide) (PHMBG) was obtained from Arch UK Biocides Ltd. (Manchester, UK), supplied as a 20 wt % aqueous solution (Cosmocil CQ) with a reported MW of 2674 and a polydispersity of 1.89. The solution was dialyzed against deionized water (MWCO 2 kDa) and lyophilized to dryness. After dialysis, the MW and polydispersity were 2810 and 1.69, respectively. The PHMBG chain on average consisted of 7.3 repeating units.

Magnetite-silica core-shell particles functionalized with PHMBG (PHMBG-M/SiO$_2$) were synthesized in three consecutive steps (FIG. 1). First, magnetite particles were prepared and were well-dispersed in water with the aid of tetramethylammonium hydroxide (TMAOH). Second, the magnetic particles were encapsulated by a shell comprising tetraethyl orthosilicate (TEOS) and epoxy-functional 3-glycidoxypropyl trimethoxysilane (GPTMS). The third step was the binding of the epoxy groups on the core-shell particle with the amine-imine groups of PHMBG. Depending on the concentration of the particles in the PHMBG grafting step, PHMBG-M/SiO$_2$ particles with varying size and biocidal activity were obtained. Thus, FeCl$_3$.6H$_2$O (7.58 g, 28 mmol) and FeCl$_2$.4H$_2$O (2.78 g, 14 mmol) were dissolved in 25 mL deionized water and the solution was brought to 80° C. under nitrogen purge within ~30 min. The solution was poured into 25 mL of 30% NH$_4$OH and the resulting black precipitate was stirred and kept at 80° C. for 1 h. The resulting particle suspension was sonicated for 1 min and separated from the supernatant by magnetocollection (magnetic field, ~1.2 T). The particles were then placed into a tube containing 30 mL of 0.33 M aqueous solution of TMAOH. The suspension was observed to be stable. The particles were separated by magnetocollection and washed twice by 50 mL of deionized water each time. The above steps were repeated three times and the resulting TMAOH-stabilized magnetite suspension fractions were combined (100 mL total, magnetite content, ~30.5 g) and diluted by 100 mL ethanol. Then, 10 mL of TEOS were added and the suspension was sonicated for 5 min, followed by addition of 10 mL of GPTMS. The suspension was kept under vigorous shaking at room temperature for 2 days, after which fractions of the suspension were conjugated with PHMBG in two different modes, resulting in two fractions of particles of varying size.

Particles of a broad range of sizes, including sub-millimeter-size, designated PHMBG-M/SiO$_2$(t), were synthesized using 190 mL of the above suspension (magnetite content, 30 g), to which a solution of 15 g PHMBG in 50 mL deionized water was added. The mixture was kept at 80° C. for 1 h, followed by shaking at 250 rpm at room temperature for 2 days. Then the product was dialyzed against an excess of deionized water (MWCO 12-14 kDa), snap-frozen and lyophilized.

Particles of smaller size, designated PHMBG-M/SiO$_2$ (s), were synthesized using 10 mL of the above suspension (magnetite content, ~0.5 g), to which a solution of 0.9 g PHMBG in 500 mL deionized water was added. The mixture was sonicated for 5 min and kept at 80° C. for 16 h, followed by shaking at 250 rpm at room temperature for 2 days.

The resulting particles were characterized by elemental analysis, TEM, dynamic light scattering (DLS), SQUID, and TGA. Elemental analysis of PHMBG-M/SiO$_2$: i) fraction designated (t): C, 25.4; H, 5.05; Fe, 19.6; N, 18.8%; ii) fraction designated (s): C, 27.8; H, 5.83; Fe, 18.3; N, 19.7%. Typical size of the PHMBG-PEI/SiO$_2$ (s) particles was observed to be approximately 150 nm; the polymer content varied in the range 60-65 wt %, and the saturation magnetization ranged from 80 to 89 emu/g of magnetite.

Example 4

Chemical Stability of the Core-Shell Magnetic Nanoparticles Described in Example 3

Representative samples of the core-shell, encapsulated PHMBG-M/SiO$_2$ (t) and non-encapsulated particles devoid of core-shell structure (PHMBG-PEI-M, known in the art—Bromberg L. et al. (2010) Binding of functionalized paramagnetic nanoparticles to bacterial lipopolysaccharides and DNA, *Langmuir*, 26(11):8829-8835) were tested for chemical stability using cyclic voltammetry (CV) and for paramagnetic properties using superconducting quantum interference device (SQUID). The CV measurements were performed with a VersaSTAT 3 potentiostat (Princeton Applied Research, Oak Ridge, Tenn.) using a 3-electrode microcell assembly (MF 1065, Bioanalytical Systems, Inc., West Lafayette, Ind.) with a carbon paste working electrode, a platinum wire auxiliary electrode, and an Ag/AgCl reference electrode filled with an aqueous 3M NaCl solution. The reference electrode adhered to the acceptable range test relative to a standard calomel electrode (SCE). The working electrode was filled with 0.2 g/g of test sample thoroughly mixed and compacted in an oil-based carbon paste (BASi CF-1010, West Lafayette, Ind.). The tip of the electrode was polished against filter paper. The electrolyte solution used in the cell was aqueous 0.1 M HCl and the CV was measured by applying a cyclic potential between ~1.5 and 2.0 V versus the Ag/AgCl electrode in 5 cycles.

SQUID measurements were performed on particle samples at two time points. The first sample was tested for its paramagnetic properties by SQUID and for iron content within 1-2 days after synthesis while being kept under a nitrogen blanket in the dry state. The second sample was placed into excess deionized water equilibrated with air, and the pH was adjusted to 7.4 using aqueous a 0.1 mM NaOH solution. The suspension was kept in sealed tubes at room temperature for about 100 months year under periodic rocking at 200 rpm. The tubes were opened once a week and purged for 10-15 min by air bubbling; the pH was checked and readjusted as necessary. A change of color in the aqueous phase of the PHMBG-PEI-M particles suspension upon aging was observed. At the end of the test, the aged suspensions were frozen at −80° C. and lyophilized to dryness. The iron content in the solids was measured by elemental analysis; paramagnetic properties were assessed by SQUID.

Figure 8:
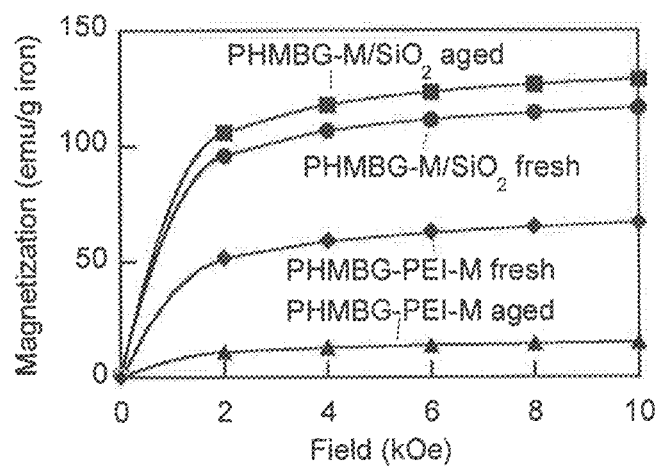
FIG. 8 depicts typical magnetization versus applied magnetic field for larger PHMBG-M/SiO$_2$ (t) and PHMBG-PEI-M particles. T=300 K. The field is shown up to 10 kOe, but in some experiments it varied from 0 to 50 kOe. Open and filled points correspond to increasing and decreasing field, respectively. In most measurements the filled and open points overlapped because the material was superparamagnetic. The magnetization is presented in emu per gram of iron. The Fe content of each type of particles was measured by elemental analysis to be 19.0, 19.6, 36.6, and 37.9 wt % in PHMBG-M/SiO$_2$ fresh, PHMBG-M/SiO$_2$ aged, PHMBG-PEI-M fresh, and PHMBG-PEI-M aged particles, respectively.

The chemical stability was tested using CV measurements (FIG. 7) and SQUID (FIG. 8). The CV measurements confirmed the chemical stability of encapsulated PHMBG-M/SiO$_2$ (t) particles against redox reactions and dissolution. Placing the encapsulated particles, either fresh or aged for 10 months, in the aggressive electrolyte (0.1 M HCl) did not generate any appreciable background current or electrode peaks characteristic of redox reactions of iron (III) and iron (II) species, indicating that virtually no iron ions were present on the particle surfaces and that the magnetite core was protected by the silica layers. Our synthesis used a one-step method of encapsulation, without the need to exchange water-immiscible organic and aqueous solvents. The electrochemical behavior of the PHMBG-PEI-M particles was strikingly different from that of the encapsulated particles in that the former particles were electroactive (generated current in the order of ~800-fold greater than their encapsulated counterparts) and exhibited current peaks.

The anodic peaks at approximately +0.6, +0.8, and +1.2 V in the first cycle of voltammograms of the PHMBG-PEI-M particles corresponded to the oxidation of Fe(II) species: $Fe^{2+} \rightarrow Fe^{3+} + e$. The cathodic peaks at 0.15-0.25 V corresponded to the Fe(III) reduction: $Fe^{3+} + e \rightarrow Fe^{2+}$. Anodic peaks in the −1 to −0.5 V area are of specific interest, as they describe the reductive dissolution behavior of the iron oxides:

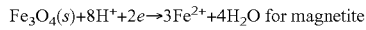

$Fe_3O_4(s) + 8H^+ + 2e \rightarrow 3Fe^{2+} + 4H_2O$ for magnetite

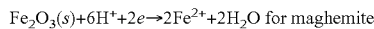

$Fe_2O_3(s) + 6H^+ + 2e \rightarrow 2Fe^{2+} + 2H_2O$ for maghemite

The cathodic peaks in the first potential scan with PHMBG-PEI-M appeared at −0.88 and −0.67 V for fresh and aged particles, respectively. The differences between the cathodic peaks due to aging are hard to ascertain quantitatively because both magnetite and other iron oxides and hydroxyoxides can be present in the aged sample. Cathodic peaks in the −0.93 to −0.88 V range are attributed to the reductive dissolution of magnetite, and their exact position depends on the particle size. From the changes in the reductive dissolution pattern of the aged PHMBG-PEI-M particles, it can be predicted that the aged particles possess a lower saturation magnetization, as all iron oxide/hydroxyoxide species possess a lower magnetization than that of magnetite.

SQUID tests were conducted along with the CV measurements. Both freshly-synthesized and aged (kept in water, pH 7.4, for 10 months in the presence of air) samples of PHMBG-M/SiO$_2$(t) and PHMBG-PEI-M particles were tested. The SQUID measurements in the increasing and decreasing magnetic field overlapped, indicating that the particles were superparamagnetic in all cases. The PHMBG-M/SiO$_2$ particles maintained their high saturation magnetization, on the order of 125-135 emu/g of iron (i.e., 80-90 emu/g of magnetite), throughout the test. The saturation magnetization of bulk magnetite is 92 emu/g. In contrast, the saturation magnetization of the PHMBG-PEI-M particles declined from approximately 80 to 18 emu/g of iron after prolonged storage in water in the presence of air. The lower magnetizations of fresh PHMBG-PEI-M particles were due to the significant volume fraction of the polymers and the existence of a well-developed polymer-metal ion surface layer with reduced magnetization on the individual nanoparticles. Therefore, the creation of the siloxane layer around individual magnetite particles in PHMBG-M/SiO$_2$ reduced the direct binding of the polymer to magnetite surface and thus enhanced the saturation magnetization. Because the PHMBG-PEI-M particles lacked this layer, the aging and oxidation of magnetite into maghemite and possibly to iron oxyhydroxides in the presence of air and amines in an aqueous environment reduced their overall magnetization. Overall, the encapsulation described herein dramatically enhanced the chemical stability of the paramagnetic particles.

Example 5

Bactericidal Properties of Core-Shell Particles Described in Example 3

The following microorganisms were used (American Type Culture Collection (ATCC), Manassas, Vir., or La Colección Española de Cultivos Tipo (CECT), Valencia, Spain): Gram-positive bacteria *Staphylococcus aureus* ATCC 25923 and ATCC 6538, *Staphylococcus epidermidis* CECT 4184, *Lactococcus lactis* ATCC 7963, *Streptococcus phocae* ATCC51973, *Lactococcus garvieae* ATCC2155, Gram-negative bacteria *Pseudomonas aeruginosa* CECT 110 and ATCC 15692, *Escherichia coli* ATCC 11229, and *Salmonella enterica* ATCC 13311. The bacteria were grown at 37° C. in Luria-Bertani (LB) broth (Sigma-Aldrich Chemical Co.) (pH 7.3), which was also used for dilutions. The mean inhibitory concentration (MIC) values of PHMBG and the particles were determined in vitro using a broth microdilution assay. The polymer or nanoparticles were dissolved or dispersed, respectively, with brief sonication; into small stock samples of sterile deionized water (10 mL, 3 mg/mL). Serial dilutions between 5 and 300 mg/L final concentration in the liquid medium were dispensed into sterile 96-well polystyrene culture Corning® Costar® cell plates (Sigma-Aldrich Chemical Co.). The diluted samples were inoculated with a suspension of the test bacterium on the liquid medium to a final concentration of approximately $10^4$ cfu/mL. The MIC was defined as the lowest concentration of PHMBG polymer, PHMBG-PEI-M or PHMBG-M/SiO$_2$ particles that inhibited bacterial growth after 0.5 h at 37° C. Measurements were conducted in triplicate. The precision of the MIC values was limited by the dilution factor and was estimated to be ±5 mg/L, Negative control experiments were conducted with the dilutions without bactericidal additives and no reduction in bacterial counts after 24 h was observed.

For testing the antiseptic properties of the core-shell magnetic nanoparticles of the invention, five Gram-positive and three Gram-negative bacteria were chosen to represent a wide range of waterborne microorganisms, all of which are pathogenic with the exception of *L. lactis*, which is extensively used in buttermilk and cheese production. Gram-positive *S. aureus* and *S. epidermidis* are well-known human pathogens; *S. phocae* is a fish and seal pathogen; and *L. garvieae* causes septicemic infections of fish and is the main risk factor for the Mediterranean European trout industry. A broth microdilution assay was carried out and the MIC was determined as the lowest additive concentration that completely inhibited the growth of the bacteria after a 24-h incubation. Both PHMBG-M/SiO$_2$ (t) and PHMBG-M/SiO$_2$ (s) particle species were tested, as well as PHMBG solutions and PHMBG-PEI-M particle suspensions. All paramagnetic nanoparticles tested exhibited strong bactericidal properties (Table 1).

TABLE 1

Minimum inhibitory concentrations (MIC), in µg/mL, for aqueous PHMBG solutions and dispersions of PHMBG-PEI-M and PHMBG-M/SiO₂ particles.

| Microorganism (Gram-positive or negative) | PHMBG | PHMBG-PEI-M | PHMBG-M/SiO₂ (t) (main sizes >250 nm) | PHMBG-M/SiO₂ (s) (main sizes <250 nm) |
|---|---|---|---|---|
| S. aureus (+) | 5 | 35 | 200 | 40 |
| S. epidermidis (+) | 0.5 | 0.005 | 200 | 15 |
| S. phocae (+) | 1.6 | 1.6 | 200 | 15 |
| L. garvieae (+) | 40 | 500 | 1000 | n.a.* |
| L. lactis (+) | 20 | 25 | 200 | 25 |
| E. coli (−) | 5 | 5 | 50 | 15 |
| S. enterica (−) | 110 | 125 | 300 | 120 |
| P. aeruginosa (−) | 30 | 40 | 1000 | 30 |

*n.a.: not available.

The MIC values for the PHMBG-PEI-M particles were in the same range as, or in the case of *S. epidermidis*, much lower than those of the PHMBG polymer, an industrial antiseptic.

Significant differences in the MIC of the PHMBG-M/SiO₂ particles, depending on their average size, were observed. The PHMBG-M/SiO₂(t) particles, which contained particles in the broad range of sizes from ~100 nm up to 0.5 mm, were several-fold (up to 30-fold in the case of *P. aeruginosa*) less effective as bactericides than their PHMBG-M/SiO₂(s) counterparts sized below ~250 nm, despite very similar chemical compositions. The average size of the PHMBG-M/SiO₂ particles affected the diameter of the inhibition zones with the particles in the disk diffusion assay. The PHMBG-PEI-M fraction composed of particles <50 nm in size was 2-3-fold more efficient in binding and killing *E. coli* than larger particles of identical chemical composition, suggesting better accessibility of the cationic groups on the smaller particles for binding *E. coli* membranes, due to the higher surface area-to-volume ratio. A similar rationale may explain the much higher efficiency of the smaller PHMBG-M/SiO₂ particles against Gram-positive bacteria, except for the fact that the particles probably bind to peptidoglycan carboxyls exposed to the external membrane surfaces in these bacteria. It has been shown that *S. aureus* is strongly negatively charged at neutral pH.

Of note, while *L. lactis* was sufficiently susceptible to PHMBG, PHMBG-M/SiO₂(s) and PHMBG-PEI-M nanoparticles, another *Lactococcus* species, *L. garvieae*, did not show comparable susceptibility. The physiologic characteristics of *L. lactis* and *L. garvieae* are described in the art as difficult to distinguish. Susceptibility toward PHMBG-modified nanoparticles is thus disclosed herein as a differentiating feature between these two pathogenic *Lactococcus* species.

Example 6

Binding, Manipulation, and Removal of Bacteria Using Paramagnetic Nanoparticles Described in Example 3

*S. aureus* (ATCC 6538) cultures were inoculated from stock cultures on tryptic soy agar slants into 100 mL of tryptic soy broth and incubated at 35° C. for 10 to 12 h. The cultures were harvested by centrifugation at 16,000×g for 10 min, and the cells were washed once, suspended, and diluted to the desired cell concentrations with the sterile-filtered Hanks' Balanced Salt solution (HBSS, pH 7.4, Sigma-Aldrich Chemical Co.). They were cultured until the mid-logarithmic phase of growth ($A_{600}$=0.3) prior to exposure to the paramagnetic particles. Suspensions of bacterial colonies (1.5×10⁶ cfu/mL, 1 mL) were mixed, with brief vortexing, in a conical 2-mL centrifuge tube containing 1 mL of HBSS buffer or paramagnetic particles suspension of a known concentration in the same buffer. The nanoparticle suspensions were briefly sonicated just prior to the cell addition. The mixed suspensions were incubated at 37° C. for 3 h with gentle shaking and the *S. aureus* cells bound to the magnetic particles were separated by placing the tube on top of a 5×5×5 mm NdFeB, Grade N52 magnet (nominal surface field, 5754 Gauss, K&J Magnetics, Inc.), in a vertical position, for 0.5 h. The cells collected on the tube's bottom were concentrated by careful pipetting of the supernatant. The isolated nanoparticle-cell aggregates were washed with 50 mM Tris-HCl buffer (200 µL×3), resuspended in 20 mL of the same buffer, and subjected to concentration determination by flow cytometry using bis-(1,3-dibutylbarbituric acid)trimethine oxonol (DiBAC4(3) stain, Molecular Probes, Inc., a division of Invitrogen) as described elsewhere. iBAC4(3) stock solution was prepared in 70% ethanol at a concentration of 1 mg/mL and stored at −20° C. The dye was added directly to the liquid sample to give a final concentration of 1 µg/mL. The samples were incubated for 2 min at room temperature before flow cytometric analysis. The same concentration determination assay was applied to the suspension of bacterial colonies just prior to their contact with the magnetic nanoparticles. The stain binds to both live and dead cells.

Capture efficiency was calculated as follows:

$$\text{capture efficiency} = 100 \times \text{Count}_2/\text{Count}_1$$

where $\text{Count}_1$ and $\text{Count}_2$ are the absolute cell counts/mL in samples before and after capture by magnetic nanoparticles; the Count values were adjusted for dilutions.

Figure 9:
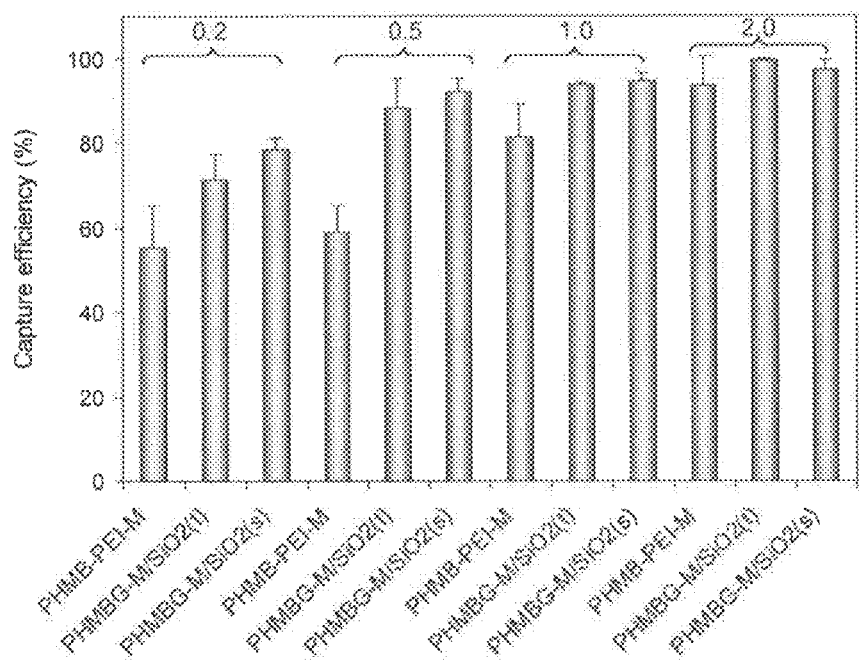
FIG. 9 depicts efficiency of *S. aureus* capture by PHMBG-modified paramagnetic particles at pH 7.4. Numbers refer to initial effective particle concentration in mg/mL.

PHMBG polymer has a $pK_a$ of 11 as well as multiple hydrophobic hexamethylene groups, and thus the PHMBG-modified magnetite particles are strong cation exchangers, capable of non-specific binding to anionic lipids in bacterial membranes. PHMBG-M/SiO₂ (t), PHMBG-M/SiO₂ (s), and PHMBG-PEI-M particles were characterized by ζ-potentials of 29.8±1.68, 34.5±1.34 and 37.8±1.11 mV, respectively, in aqueous 10 mM KCl at 25° C. Gram-positive bacteria binding was characterized by a direct assay of *S. aureus* removal from the suspensions by magnetocollection. As shown in FIG. 9, the capture efficiency of the particles depended on their initial concentration, but even with the particle concentration of 0.1 mg/mL the efficiency exceeded 50% in all cases, with PHMBG-M/SiO₂ particles reaching 98-99%. The encapsulated PHMBG-M/SiO₂ particles were more efficient in the removal of *S. aureus* than their non-encapsulated counterparts at all particle concentrations, probably due to the higher saturation magnetization that increased the efficiency of magnetocollection. At lower concentrations, the PHMBG-M/SiO₂ (s) particles with smaller average diameter were discernibly more efficient than larger PHMBG-M/SiO₂ (t) in capturing and removing the cells, probably due to the higher surface area (and thus the greater number of available PHMBG chains) per particle weight. The particle size appeared to play a significant role in the ability of the particles to kill bacteria.

The ability of the particles to move the Gram-positive bacteria cells was also explored. All tested particle fractions moved rapidly under strong magnetic fields and could be delivered to small areas where the bacteria had been located. *S. aureus* were incubated in a Petri dish and allowed to adhere to the center of the bottom of the dish for 8 h. A strong NdFeB magnet (5×5×5 mm) was placed under the center of the Petri dish, followed by the addition of particles. The resulting particle concentration in the dish was 0.1 wt %. With gentle agitation, the particles were attracted to the center of the Petri dish by the magnetic field, where they killed the bacteria. These experiments demonstrated the possibility of directing and manipulating the particles by magnets, which might be useful in such applications as the clearing of tanks, pipes, and other reservoirs with hard-to-reach areas.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A particle, comprising a plurality of magnetic nanoparticles, and a silicon oxide shell surrounding the plurality of magnetic nanoparticles, wherein the silicon oxide shell integrally comprises a plurality of functionalized alkyl silanes, wherein each functionalized alkyl silane comprises a reactive functional group which is an electrophilic group.

2. The particle of claim 1, wherein the magnetic nanoparticles comprise magnetite.

3. The particle of claim 1, wherein the electrophilic group is selected from the group consisting of epoxy, alkyl halide, ester, aldehyde, and ketone.

4. A particle, represented by (MS)-$L^1$-X-$L^2$-$FG^3$, wherein
(MS) is a particle comprising a plurality of magnetic nanoparticles and a silicon oxide shell surrounding the plurality of magnetic nanoparticles;
$L^1$ is an alkyl or alkyloxy linker moiety integral to the silicon oxide shell;
$L^2$ is an alkyl or alkyloxy linker moiety;
X is a covalent linkage, joining $L^1$ and $L^2$, selected from the group consisting of

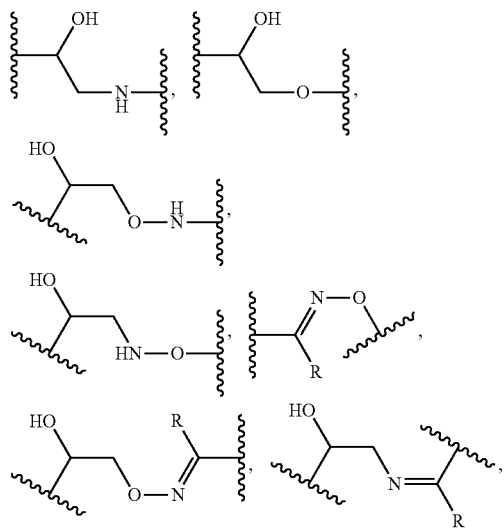

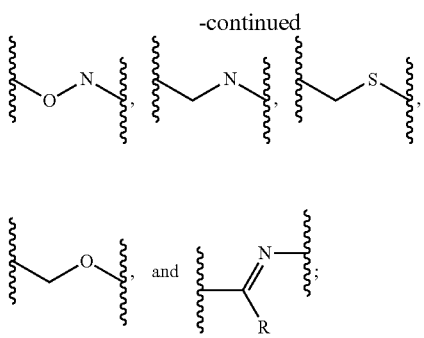

$FG^3$ is a reactive functional group which is an electrophilic group covalently linked to $L^2$; and
R is H or alkyl.

5. The particle of claim 4, wherein the magnetic nanoparticles comprise magnetite.

6. The particle of claim 4, wherein the electrophilic group is selected from the group consisting of epoxy, alkyl halide, ester, aldehyde, and ketone.

7. The particle of claim 4, wherein $L^2$-$FG^3$ is a polymer.

8. A method for producing a particle, comprising combining (i) an aqueous solution of magnetic nanoparticles, (ii) a reactive silicate, and (iii) a functionalized alkyl silane comprising a first reactive functional group which is an electrophilic group, under conditions permitting formation of a silicon oxide shell surrounding the magnetic nanoparticles and integrally comprising the functionalized alkyl silane.

9. The method of claim 8, further comprising linking the functionalized alkyl silane to a molecule comprising a second reactive functional group through a covalent bond formed by reaction of the first reactive functional group with the second reactive functional group, wherein the second reactive functional group is (i) complementary to the first reactive functional group and (ii) a nucleophilic group.

10. A method of separation, comprising combining a substance of interest, an effective amount of a particle of claim 1, and a solvent, thereby forming a mixture comprising a complex comprising the substance of interest and the particle; and applying to the mixture a magnetic field of effective strength to influence mobility of the complex in the mixture.

11. A method of separation, comprising combining a substance of interest, an effective amount of a particle of claim 4, and a solvent, thereby forming a mixture comprising a complex comprising the substance of interest and the particle; and applying to the mixture a magnetic field of effective strength to influence mobility of the complex in the mixture.

12. A method of killing a bacterium, comprising combining a bacterium, an effective amount of a particle of claim 4, and a solvent, thereby forming a mixture comprising a complex comprising the bacterium and the particle.

13. The particle of claim 4, wherein X is
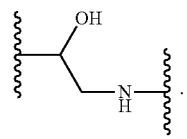
* * * * *